United States Patent
Campbell et al.

(10) Patent No.: US 7,223,772 B1
(45) Date of Patent: May 29, 2007

(54) PYRAZOLOPYRIDINE DERIVATIVES AS SELECTIVE COX-2 INHIBITORS

(75) Inventors: Ian Baxter Campbell, Broom (GB); Alan Naylor, Royston (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/830,836

(22) PCT Filed: Nov. 1, 1999

(86) PCT No.: PCT/EP99/08186

§ 371 (c)(1),
(2), (4) Date: May 1, 2001

(87) PCT Pub. No.: WO00/26216

PCT Pub. Date: May 11, 2000

(30) Foreign Application Priority Data

Nov. 3, 1998 (GB) .............................. 9824062
Sep. 3, 1999 (GB) .............................. 9920909

(51) Int. Cl.
*A61K 31/415* (2006.01)
*A61K 31/44* (2006.01)
*C07D 231/56* (2006.01)
*C07D 471/02* (2006.01)

(52) U.S. Cl. .................... 514/300; 548/362.5; 546/119; 514/406

(58) Field of Classification Search .............. 548/362.5; 514/406, 300; 546/119
See application file for complete search history.

(56) References Cited

U.S. PATENT DOCUMENTS

| | | | |
|---|---|---|---|
| 4,985,444 | A | 1/1991 | Shiokawa et al. |
| 5,155,114 | A | 10/1992 | Shiokawa et al. |
| 5,296,490 | A | 3/1994 | Shiokawa et al. |
| 5,300,478 | A | 4/1994 | Michaely et al. |
| 5,498,774 | A | 3/1996 | Mitsudera et al. |
| 5,552,422 | A | 9/1996 | Gauthier et al. |
| 5,700,816 | A | 12/1997 | Isakson et al. |
| 5,990,148 | A | 11/1999 | Isakson et al. |
| 6,136,839 | A | 10/2000 | Isakson et al. |

FOREIGN PATENT DOCUMENTS

| | | |
|---|---|---|
| EP | 0404 190 A1 | 12/1990 |
| EP | 0404 190 B1 | 12/1990 |
| EP | 0467248 B1 | 1/1992 |
| WO | 0364204 A1 | 4/1990 |
| WO | WO 9100092 | 1/1991 |
| WO | WO 9119497 | 12/1991 |
| WO | WO 95/00501 | 1/1995 |
| WO | WO96 06840 A | 3/1996 |
| WO | WO96 21667 A | 7/1996 |
| WO | WO96 31509 A | 10/1996 |
| WO | WO 9641625 | 12/1996 |
| WO | WO 9641626 | 12/1996 |
| WO | WO 9641645 | 12/1996 |
| WO | WO99 12930 A | 3/1999 |
| WO | WO 0114375 | 3/2001 |

OTHER PUBLICATIONS

Kakehi, et. al, "Preparation of New Nitrogen–Bridged Heterocycles. 18. Facile Formations of 3–Arylpyrazolo [1,5–a] pyridines and 1–Arylindolizines", Bull. Chem. Soc. Jpn. 61, 2055–2061, 1988.*

Akahane, A. et al., "Discovery of 6–Oxo–3–(2–phenylpyrazolo [1,5–a]pyridin–3–yl)–1(6H)–pyridazinebutanoic Acid (FK 838): A Novel Non–Xanthine Adenosine $A_1$ Receptor Antagonist with Potent Diuretic Activity", Journal of Medicinal Chemistry, vol. 42, No. 5, 11 Mar. 1999, pp. 779–784.

Talley, John J., *Progress in Medicinal Chemistry*, vol. 36, (1999), pp. 201–234.

Vane, John, *Nature*, vol. 367: (1994) pp. 215–216.

Therien, M., et al: "Synthesis and Biological Evaluation of 5,6–diarylimidazo' 2.1–b!thiazole as Selective COX–2 Inhibitors", Bioorganic & Medicinal Chemistry Letters, GB, Oxford, vol. 7, No. 1, Jan. 7, 1997, pp. 47–52.

Roy, P., et al: "A New Series of Selective COX–2 Inhibitors: 5,6–diarylthiazolo'3,2–b!'1,2,4!triazoles", Bioorganic & Medicinal Chemistry Letters, GB, Oxford, vol. 7, No. 1, Jan. 7, 1997, pp. 57–62.

Talley, J. J.: "Selective Inhibitors of Cyclooxygenase–2", Expert Opinion on Therapeutic Patents, GB, Ashley Publications, vol. 7, No. 1, Jan. 1, 1997, pp. 55–62.

Carter, J. S.: "Recently Reported Inhibitors of Cyclooxygenase–2", Expert Opinion on Therapeutic Patents, GB, Ashley Publications, vol. 8, No. 1, Jan. 1, 1998, pp. 21–29.

* cited by examiner

*Primary Examiner*—Alan L. Rotman
*Assistant Examiner*—Binta Robinson
(74) *Attorney, Agent, or Firm*—J. Scott Young

(57) ABSTRACT

The invention provides the compounds of formula (I)   (I)

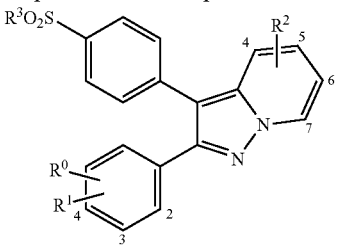

and pharmaceutically acceptable derivatives thereof wherein:

$R^0$ and $R^1$ are independently selected from the group consisting of H, halogen, $C_{1-6}$alkyl, $C_{1-6}$alkoxy, and $C_{1-6}$alkoxy substituted by one or more fluorine atoms;

$R^2$ is selected from the group consisting of H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, and $C_{1-6}$alkoxy substituted by one or more fluorine atoms; and $R^3$ is $C_{1-6}$alkyl or $NH_2$.

Compounds of formula (I) are potent and selective inhibitors of COX-2 and are of use in the treatment of the pain, fever, inflammation of a variety of conditions and diseases.

29 Claims, No Drawings

PYRAZOLOPYRIDINE DERIVATIVES AS SELECTIVE COX-2 INHIBITORS

CROSS-REFERENCES TO RELATED APPLICATIONS

This application is a Rule 371 Application of PCT Application No. EP99/08186, filed 1 Nov. 1999, which claims priority to GB Application Serial No. 9824062.5, filed 3 Nov. 1998 and GB Application Serial No. 9920909.0, filed 3 Sep. 1999.

BACKGROUND OF THE INVENTION

This invention relates to pyrazolo[1,5-a]pyridine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is responsible for the important physiological functions such as maintenance of gastrointestinal integrity and renal blood flow. In contrast the inducible form, COX-2, is believed to be responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

DETAIL DESCRIPTION OF THE INVENTION

The invention thus provides the compounds of formula (I)

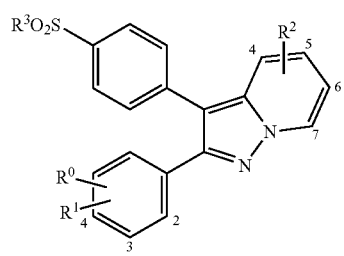

(I)

and pharmaceutically acceptable derivatives thereof in which:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, C(O)H, C(O)$C_{1-6}$alkyl, $C_{1-6}$alkylsulphonyl, $C_{1-6}$alkoxy substituted by one or more fluorine atoms; and $R^3$ is $C_{1-6}$alkyl or $NH_2$.

By pharmaceutically acceptable derivative is meant any pharmaceutically acceptable salt, solvate, ester or amide, or salt or solvate of such ester or amide, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides.

Acylated benzenesulphonamide derivatives are of especial interest. Examples of such benzenesulphonamide derivatives include:
N-alkylcarbonylbenzenesulphonamides;
N-alkoxyalkylcarbonylbenzenesulphonamides;
N-alkoxycarbonylbenzenesulphonamides;
N-arylcarbonylbenzenesulphonamides;
N-alkoxycarbonylalkylcarbonylbenzenesulphonamides
N-carboxylalkylcarbonylbenzenesulphonamides
N-alkylcarbonyloxyalkylcarbonylbenzenesulphonamides;
N-alkylaminoalkylcarbonylbenzenesulphonamides; and
N-dialkylaminoalkylcarbonylbenzenesulphonamides.

With reference to such benzenesulphonamide derivatives, and by way of example only, alkyl may be $C_{1-6}$alkyl or $C_{1-6}$alkyl substituted by one or more halogen (e.g. chlorine) atoms; alkoxy may be $C_{1-6}$alkoxy or $C_{1-6}$alkoxy substituted by one or more halogen (e.g. chlorine) atoms; and aryl may be phenyl or substituted phenyl.

It will be appreciated by those skilled in the art that the pharmaceutically acceptable derivatives of the compounds of formula (I) may be derivatised at more than one position.

It will be further appreciated by those skilled in the art that benzenesulphonamide derivatives of formula (I) may be useful as intermediates in the preparation of compounds of formula (I), or as pharmaceutically acceptable derivatives of formula (I), or both.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts include: acid addition salts formed with inorganic or organic acids, preferably inorganic acids, e.g. hydrochlorides, hydrobromides and sulphates; and alkali metal salts, formed from addition of alkali metal bases, such as alkali metal hydroxides, e.g. sodium salts.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

In one aspect of the invention $R^0$ is at the 3- or 4-position of the phenyl ring, as defined in formula (I).

In another aspect of the invention $R^2$ is at the 6-position of the pyrazolopyridine ring, as defined in formula (I).

In another aspect of the invention $R^0$ and $R^1$ are independently H, halogen, $C_{1-6}$alkyl, or $C_{1-6}$alkoxy.

In another aspect of the invention $R^2$ is $C_{1-6}$alkyl substituted by one or more fluorine atoms.

In another aspect of the invention $R^3$ is $C_{1-3}$alkyl or $NH_2$.

Within the invention there is provided one group of compounds of formula (I) (group A) wherein: $R^0$ and $R^1$ are independently H, halogen, $C_{1-6}$alkyl, or $C_{1-6}$alkoxy; $R^2$ is $C_{1-3}$alkyl substituted by one or more fluorine atoms; and $R^3$ is $C_{1-3}$alkyl or $NH_2$.

Within group A, there is provided a further group of compounds (group A1) wherein: $R^0$ and $R^1$ are independently H, F, Cl, $C_{1-3}$alkyl (e.g. methyl), or $C_{1-3}$alkoxy (e.g. ethoxy); $R^2$ is $C_{1-3}$alkyl substituted by one or more fluorine atoms (e.g. trifluoromethyl); and $R^3$ is methyl or $NH_2$.

Within group A1, there is provided a further group of compounds (group A2) wherein: $R^0$ is F, Cl, or $C_{1-3}$alkyl (e.g. methyl) or $C_{1-3}$alkoxy (e.g. ethoxy); $R^1$ is H; $R^2$ is $C_{1-3}$alkyl substituted by one or more fluorine atoms (e.g. trifluoromethyl); and $R^3$ is methyl or $NH_2$.

Within groups A, A1 and A2 there are provided further groups of compounds wherein $R^0$ is at the 3- or 4-position of the phenyl ring, and $R^2$ is at the 6-position of the pyrazolopyridine ring, as defined in formula (I).

Within the invention there is provided another group of compounds of formula (I) (group B) wherein: $R^0$ and $R^1$ are independently H, halogen, $C_{1-6}$alkyl, or $C_{1-6}$alkoxy; $R^2$ is $C_{1-3}$alkyl; and $R^3$ is $C_{1-3}$alkyl or $NH_2$.

Within group B, there is provided a further group of compounds (group B1) wherein: $R^0$ and $R^1$ are independently H, F, or $C_{1-3}$alkoxy (e.g. ethoxy); $R^2$ is $C_{1-3}$alkyl (e.g. methyl); and $R^3$ is methyl or $NH_2$.

Within group B1, there is provided a further group of compounds (group B2) wherein: $R^0$ is H, F, or $C_{1-3}$alkoxy (e.g. ethoxy); $R^1$ is H; $R^2$ is $C_{1-3}$alkyl (e.g. methyl); and $R^3$ is methyl or $NH_2$.

Within groups B, B1 and B2 there are provided further groups of compounds wherein $R^0$ is at the 3- or 4-position of the phenyl ring, and $R^2$ is at the 6-position of the pyrazolopyridine ring, as defined in formula (I).

It is to be understood that the present invention encompasses all isomers of the compounds of formula (I) and their pharmaceutically acceptable derivatives, including all geometric, tautomeric and optical forms, and mixtures thereof (e.g. racemic mixtures).

In one aspect the invention provides the following compounds:
4-[2-(3-fluoro-phenyl)-6-trifluoromethyl-pyrazolo[1,5-a]pyridin-3-yl]benzenesulfonamide;
2-(3-fluoro-phenyl)-3-(4-methanesulfonyl-phenyl)-6-trifluoromethyl-pyrazolo[1,5-a]pyridine;
4-[2-(4-ethoxy-phenyl)-6-trifluoromethyl-pyrazolo[1,5-a]pyridin-3-yl]benzenesulfonamide;
4-[2-(4-fluoro-phenyl)-6-trifluoromethyl-pyrazolo[1,5-a]pyridin-3-yl]benzenesulfonamide;
2-(4-fluoro-phenyl)-3-(4-methanesulfonyl-phenyl)-6-trifluoromethyl-pyrazolo[1,5-a]pyridine;
4-(2-phenyl-6-trifluoromethyl-pyrazolo[1,5-a]pyridin-3-yl)-benzenesulfonamide;
3-(4-methanesulfonyl-phenyl)-2-phenyl-6-trifluoromethyl-pyrazolo[1,5-a]pyridine;
4-[2-(4-methyl-phenyl)-6-trifluoromethyl-pyrazolo[1,5-a]pyridin-3-yl]benzenesulfonamide;
and pharmaceutically acceptable derivatives thereof.

In another aspect the invention provides the following compounds:
N-acetyl-4-[2-(3-fluorophenyl)-6-(trifluoromethyl)pyrazolo[1,5-a]pyridin-3-yl]benzenesulfonamide;
N-acetyl-4-[2-(4-ethoxyphenyl)-6-(trifluoromethyl)pyrazolo[1,5-a]pyridin-3-yl]benzenesulfonamide;
N-acetyl-4-[2-phenyl-6-(trifluoromethyl)pyrazolo[1,5-a]pyridin-3-yl]benzenesulfonamide;
sodium salt of N-acetyl-4-[2-(3-fluorophenyl)-6-(trifluoromethyl)pyrazolo[1,5-a]pyridin-3-yl]benzenesulfonamide;
4-[2-(3-fluorophenyl)-6-(trifluoromethyl)pyrazolo[1,5-a]pyridin-3-yl]-N-(2-methoxyacetyl)benzenesulfonamide;
4-[2-(3-fluorophenyl)-6-(trifluoromethyl)pyrazolo[1,5-a]pyridin-3-yl]-N-propionylbenzenesulfonamide;
4-[2-(3-fluorophenyl)-6-(trifluoromethyl)pyrazolo[1,5-a]pyridin-3-yl]-N-isobutyrylbenzenesulfonamide;
N-benzoyl-4-[2-(3-fluorophenyl)-6-(trifluoromethyl)pyrazolo[1,5-a]pyridin-3-yl]benzenesulfonamide;
methyl 4-[({4-[2-(3-fluorophenyl)-6-(trifluoromethyl)pyrazolo[1,5-a]pyridin-3-yl]phenyl}sulfonyl)amino]-4-oxobutanoate;
4-[({4-[2-(3-fluorophenyl)-6-(trifluoromethyl)pyrazolo[1,5-a]pyridin-3-yl]phenyl}sulfonyl)amino]-4-oxobutanoic acid;
4-[2-(3-fluorophenyl)-6-(trifluoromethyl)pyrazolo[1,5-a]pyridin-3-yl]-N-pentanoylbenzenesulfonamide;
2-[({4-[2-(3-fluorophenyl)-6-(trifluoromethyl)pyrazolo[1,5-a]pyridin-3-yl]phenyl}sulfonyl)amino]-2-oxoethyl acetate;
N-acetyl-4-[2-(4-fluorophenyl)-6-(trifluoromethyl)pyrazolo[1,5-a]pyridin-3-yl]benzenesulfonamide;
N-(2-chloroacetyl)-4-[2-(3-fluorophenyl)-6-(trifluoromethyl)pyrazolo[1,5-a]pyridin-3-yl]benzenesulfonamide;
N-[2-(diethylamino)acetyl]-4-[2-(3-fluorophenyl)-6-(trifluoromethyl)pyrazolo[1,5-a]pyridin-3-yl]benzenesulfonamide;
methyl{4-[2-(3-fluorophenyl)-6-(trifluoromethyl)pyrazolo[1,5-a]pyridin-3-yl]phenyl}sulfonylcarbamate; and
tert-butyl{4-[2-(3-fluorophenyl)-6-(trifluoromethyl)pyrazolo[1,5-a]pyridin-3-yl]phenyl}sulfonylcarbamate.

In a further aspect the invention provides the following compounds:
4-[6-chloro-2-(3-ethoxyphenyl)pyrazolo[1,5-a]pyridin-3-yl]benzenesulfonamide;
6-chloro-2-(3-ethoxyphenyl)-3-[4-(methylsulfonyl)phenyl]pyrazolo[1,5-a]pyridine;
4-[6-methyl-2-phenyl-pyrazolo[1,5-a]pyridin-3-yl]benzenesulfonamide;
4-[2-(3-fluorophenyl)-6-methyl-pyrazolo[1,5-a]pyridin-3-yl]benzenesulfonamide;
4-[2-(3-ethoxyphenyl)-6-methyl-pyrazolo[1,5-a]pyridin-3-yl]benzenesulfonamide;
4-[2-(4-ethoxyphenyl)-6-methyl-pyrazolo[1,5-a]pyridin-3-yl]benzenesulfonamide;
6-methyl-2-phenyl-3-[4-(methylsulfonyl)phenyl]pyrazolo[1,5-a]pyridine;
2-(3-fluorophenyl)-6-methyl-3-[4-(methylsulfonyl)phenyl]pyrazolo[1,5-a]pyridine;
2-(3-ethoxyphenyl)-6-methyl-3-[4-(methylsulfonyl)phenyl]pyrazolo[1,5-a]pyridine;
2-(4-ethoxyphenyl)-6-methyl-3-[4-(methylsulfonyl)phenyl]pyrazolo[1,5-a]pyridine;
and pharmaceutically acceptable derivatives thereof.

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; neuropathic pain (e.g. neuralgia, such as post herpetic neuralgia, trigeminal neuralgia and sympathetically maintained pain); synovitis;

arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by selective inhibition of COX-2.

According to a further aspect of the invention, we provide a method of treating a human or animal subject suffering from a condition which is mediated by selective inhibition of COX-2 which comprises administering to said subject an effective amount of a compound of formula (I) or a pharmaceutically acceptable derivative.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by selective inhibition of COX-2.

According to another aspect of the invention, we provide the use of a compound of formula (I) or a pharmaceutically acceptable derivative thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include pain relievers such as a glycine antagonist, a sodium channel inhibitor (e.g. lamotrigine), a substance P antagonist (e.g. an $NK_1$ antagonist), acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor α; an antibody therapy (e.g. a monoclonal antibody therapy); a stimulant, including caffeine; an $H_2$-antagonist, such as ranitidine; a proton pump inhibitor, such as omeprazole; an antacid, such as aluminium or magnesium hydroxide; an antiflatulent, such as simethicone; a decongestant, such as phenylephrine, phenylpropanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine. It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below. In the discussion and formulae that follow $R^0$ to $R^3$ are as defined in formula (I) above unless otherwise stated; Hal is a halogen, such as Br or I; $X^-$ is a counterion, such as $I^-$; NBS is N-bromosuccinimide; NCS is N-chlorosuccinimide; DMF is N,N-dimethylformamide; and alkyl and halogen are as previously defined.

Thus according to a first process (A), compounds of formula (I) may be prepared by reacting a compound of formula (II)

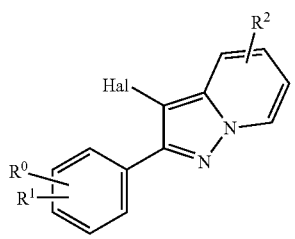

(II)

with a boronic acid of formula (III)

(III)

or a suitable derivative thereof in the presence of a suitable transition metal catalyst. Suitable derivatives of formula (III) include boronic acid esters, such as those described in R. Miyaura et al, J. Org. Chem., 1995, 60, 7508–7510.

Conveniently, the reaction is carried out in a solvent, such as an ether (e.g. 1,2-dimethoxyethane); in the presence of a base, such as an inorganic base (e.g. sodium carbonate); and employing a palladium catalyst, such as tetrakis (triphenylphosphine)palladium(0).

According to a another process (B), compounds of formula (I) wherein $R^3$ is $C_{1-6}$alkyl may be prepared by oxidising a compound of formula (IV)

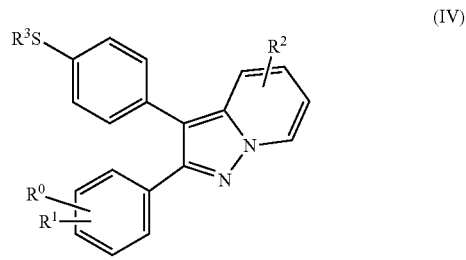

(IV)

under conventional conditions. Conveniently the oxidation is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

According to a another process (C), compounds of formula (I) wherein $R^2$ is $C_{1-6}$alkylsulphonyl may be prepared by oxidising a compound of formula (V)

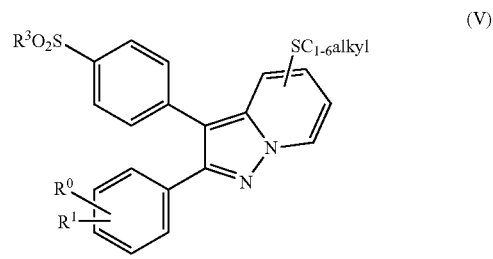

(V)

under conventional conditions. Conveniently the oxidation is effected in the manner described just above for process (B).

According to a another process (D), compounds of formula (I) wherein $R^2$ is $C_{1-6}$alkoxy substituted by one or more fluorine atoms may be prepared by reacting a phenol of formula (VI)

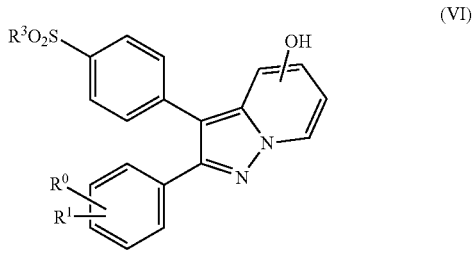

(VI)

with a halofluoroalkane under conventional conditions. Conveniently the reaction is effected in a solvent, such as a polar solvent (e.g. DMF), in the presence of a strong base, such as an inorganic hydride (e.g. sodium hydride), at about ambient temperature and using the appropriate bromofluoroalkane to give the desired compound of formula (I).

According to a another process (E), compounds of formula (I) wherein $R^3$ is $NH_2$ may be prepared by reacting a compound of formula (X)

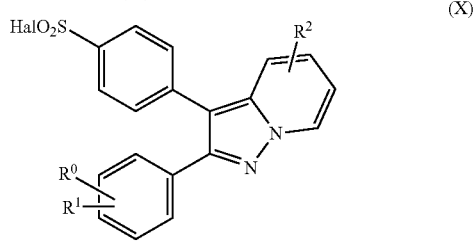

(X)

with a source of ammonia under conventional conditions. Conveniently the reaction is carried out in a solvent, such as an ester (e.g. ethyl acetate); at ambient or elevated temperature (e.g. ambient temperature); employing ammonium hydroxide as the source of ammonia and using a compound of formula (X) where Hal is Cl.

According to another process (F) compounds of formula (I) may be prepared by interconversion, utilising other compounds of formula (I) as precursors. The following procedures are illustrative of suitable interconversions.

Compounds of formula (I) wherein $R^2$ represents $C_{1-6}$alkyl substituted by one or more fluorine atoms may be prepared from the appropriate compound of formula (I) wherein $R^2$ is $C_{1-6}$hydroxyalkyl, C(O)H or C(O)$C_{1-6}$alkyl, by treatment with a suitable source of fluorine. Suitable sources of fluorine include, for example, (diethylamino) sulphur trifluoride. Conveniently the reaction is effected in the presence of a solvent, such as a halogenated hydrocarbon (e.g. dichloromethane), and at reduced temperature, such as −78° C.

Compounds of formula (I) wherein $R^2$ represents C(O)H may be prepared from the corresponding compound of formula (I) wherein $R^2$ represents $CH_2OH$ by oxidation. Suitable oxidising agents include, for example, manganese (IV) oxide. Conveniently the oxidation is effected in the presence of a solvent, such as a halogenated hydrocarbon (e.g. chloroform), and at elevated temperature (e.g. under reflux).

Compounds of formula (I) wherein $R^2$ represents $C_{1-6}$hydroxyalkyl, and wherein the hydroxy group is attached to the carbon linked to the pyridine ring, may be prepared by reduction of the compound of formula (I) wherein $R^2$ represents the corresponding aldehyde or ketone. Suitable reducing agents include hydride reducing agents, such as diisobutylaluminium hydride. Conveniently the reduction is effected in the presence of a solvent, such as a halogenated hydrocarbon (e.g. dichloromethane), and at reduced temperature, such as −78° C.

As will be appreciated by those skilled in the art it may be necessary or desirable at any stage in the synthesis of compounds of formula (I) to protect one or more sensitive groups in the molecule so as to prevent undesirable side reactions.

Another process (G) for preparing compounds of formula (I) thus comprises deprotecting protected derivatives of compounds of formula (I).

The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Acylation of compounds of formula (I) wherein $R^3$ is $NH_2$ to provide corresponding acylated benzenesulphonamide derivatives may be carried out by conventional means, for example by employing conventional acylating agents such as those described in 'Advanced Organic Chemistry' by J March, fourth edition, (John Wiley and Sons, 1992), pp 417–424, incorporated herein by reference.

Compounds of formula (II) may be prepared by halogenating compounds of formula (VII)

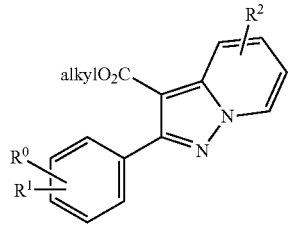

(VII)

by conventional means.

Thus esters of formula (VII) are first hydrolysed to their corresponding acids, for example by treatment with a strong base (e.g. sodium hydroxide), in the present of a solvent (e.g. ethanol) and at elevated temperature. The corresponding acid is then treated with a halogenating agent, conveniently at ambient temperature and in a solvent (e.g. chlorinated hydrocarbon), under which conditions the acid undergoes both halogenation and decarboxylation. Conveniently, the halogenating agent is a brominating agent, such as bromine in the presence of a strong acid (e.g. hydrobromic acid in acetic acid) or NBS, to yield the corresponding compound of formula (II) wherein Hal is bromine.

Esters of formula (VII) may be prepared by reacting a compound of formula (VIII)

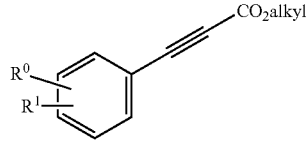

(VIII)

with an aminopyridinium complex of formula (IX)

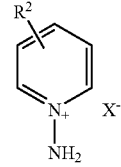

(IX)

under conventional conditions. Conveniently the reaction is effected in the presence of a base, such as potassium carbonate, a solvent, such as DMF and at ambient temperature.

Compounds of formula (II) may also be prepared by halogenating a compound of formula (XI)

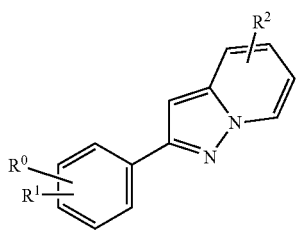

(XI)

by conventional means. Conveniently the halogenation is effected using a brominating agent (e.g. NBS), at ambient temperature and in a solvent (e.g. chlorinated hydrocarbon), to yield the corresponding compound of formula (II)

wherein Hal is bromine. Compounds of formula (XI) may be prepared from an azirine of formula (XII)

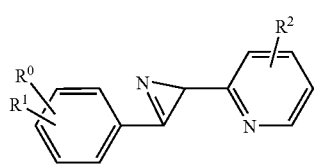

by conventional means. Conveniently the reaction is effected in a solvent, such as an aromatic hydrocarbon (e.g. 1,2,4-trichlorobenzene) and at elevated temperature (e.g. under reflux).

Compounds of formula (XII) may be prepared from an oxime of formula (XIII)

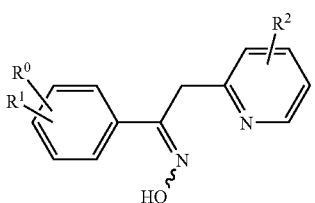

by conventional means. Conveniently the oxime is dissolved in a solvent such as a haloalkane (e.g. dichloromethane), treated a with a base, such as an amine (e.g. triethylamine), the mixture cooled to about 0° C. and treated with an anhydride (e.g. trifluoroacetic anhydride), and the mixture then allowed to warm to ambient temperature.

Compounds of formula (XIII) may be prepared from a ketone of formula (XIV)

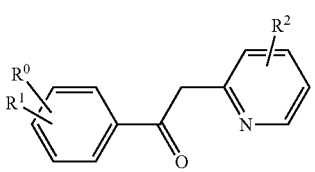

by conventional means. Conveviently the reaction is effected with hydroxylamine or a salt thereof (e.g. hydroxylamine hydrochloride), in a solvent such as an alcohol (e.g. methanol) and at ambient temperature.

Compounds of formula (XIV) may be prepared by reacting a compound of formula (XV)

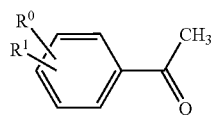

with a compound of formula (XVI)

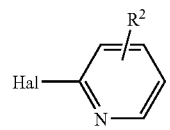

under conventional conditions. Conveviently the compound of formula (XVI) is a chloro derivative and the reaction is effected in the presence of a strong base, such as an inorganic hydride (e.g. sodium hydride) and at about ambient temperature.

Boronic acids of formula (III) are either known compounds or may be prepared by literature methods such as those described in, for example, EPA publication No. 533268.

Compounds of formula (X) may be prepared by sulphonylating a compound of formula (XVII)

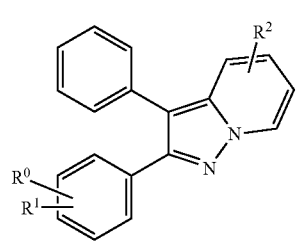

under conventional conditions. Conveniently the sulphonylation is effected using sulphonic acid or a derivative thereof, such as a halosulphonic acid (e.g. chlorosulphonic acid); in the presence of a solvent, such as a halogenated alkane (e.g. dichloromethane); and at between −78° C. and ambient temperature (e.g. −70° C.).

Compounds of formulae (IV), (V) and (VI) and (XVII) may be prepared by methods analogous to those described for the preparation of the corresponding compounds of formula (I).

Compounds of formulae (VIII), (IX), (XV), (XVI) are either known compounds or may be prepared by literature methods such as those described in, for example:

D H Wadsworth et al, J Org Chem, (1987), 52(16), 3662–8;

J Morris and D G Wishka, Synthesis, (1994), (1), 43–6;

Y Kobayashi et al, Chem Pharm Bull, (1971), 19(10), 2106–15;

K Novitskii et al, Khim Geterotskil Soedin, (1970) 2, 57–62; and

T Tsuchiya, J Kurita and K Takayama, Chem Pharm Bull, (1980), 28(9) 2676–81;

all incorporated herein by reference.

Certain intermediates described above are novel compounds, and it is to be understood that all novel intermediates herein form further aspects of the present invention. Compounds of formulae (II), (IV), (X) and (XVII) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples illustrate the invention but do not limit the invention in any way. All temperatures are in ° C. Flash column chromatography was carried out using Merck 9385 silica. Solid Phase Extraction (SPE) chromatography was carried out using Varian Mega Bond Elut (Si) cartridges (Anachem) under 15 mmHg vacuum with stepped gradient elution. Thin layer chromatography (Tlc) was carried out on silica plates. NMR was carried out on a Brucker 400 MHz spectrometer. Chemical shifts are given, with respect to tetramethylsilane as internal chemical shift reference, in δ ppm. In addition to those already defined, the following abbreviations are used: Me, methyl; DMSO, dimethylsulphoxide; TFA, trifluoroacetic acid; DME, dimethoxyethane; THF, tetrahydrofuran; DCM, dichloromethane; M, molar; s, singlet; d, doublet; t, triplet; m, multiplet; and br, broad.

EXAMPLE 1

4-[2-(3-Fluoro-phenyl)-6-trifluoromethyl-pyrazolo [1,5-a]pyridin-3-yl]benzenesulfonamide i) 3-Trifluoromethyl-pyridin-1-ylideneamine 2,4,6-trimethylphenylsulphonate Solid t-butoxycarbonyl-O-mesitylenesulfonylhydroxylamine (13.44 g, 42.5 mmol)[1] was added portionwise with stirring to TFA (40 ml) over 10 minutes then stirred for a further 30 minutes. The solution was poured onto ice (~250 ml) and left until the ice melted. The resulting white solid was filtered off, washed with water, and dissolved in DME (200 ml). The solution was dried over 4 Å mol. sieves for 1.5 hours, filtered, then 3-trifluoromethylpyridine (5 g, 34 mmol) added and the reaction stirred at ambient temperature for 20 h. The intermediate salt was isolated by filtration, washed with DME to give the title compound as a white solid (6.63 g, 54%). 1H NMR δ (DMSO) 9.34 (1H, s); 9.0 (1H, d, J 6 Hz); 8.8 (2H, br s); 8.68 (1H, d, J 8 Hz); 8.22 (1H, t, J 7 Hz); 6.75 (2H, s); 2.17 (3H, s).

Ref 1 Josef G Krause, Synthesis, 1972, 140 ii) 1-(2,2-Dibromo-vinyl)-3-fluoro-benzene

To a stirred, cooled (ice/salt, 0°) solution of carbon tetrabromide (48.82 g) in anhydrous DCM (200 ml) was added, portionwise over 3 minutes, triphenylphosphine (77.1 g), maintaining the temperature below 10°. The resulting orange suspension was stirred at 0° for 1 hour before adding to it 3-fluorobenzaldehyde (7.8 ml). After the addition was complete, the suspension was stirred at 0° for 1 hour then quenched by the addition of water (75 ml). The organic phase was separated and washed with brine (75 ml), dried ($Na_2SO_4$) and evaporated to dryness. The residue was poured into cyclohexane (1 L) and stirred for 30 minutes. The organic phase was decanted and the residue taken up into DCM and poured into cyclohexane (1 L). This procedure was repeated twice more and the combined organic phases concentrated to ~100 ml and passed through silica gel. The filtrate was concentrated to give the title compound as a mobile yellow oil (24 g, 100%). MH+ 280, MH− 279

NMR ($CDCl_3$) δ 7.05 (1H, tm, J=9 Hz) 7.3 (3H, m) 7.45 (1H, s).

iii) (3-Fluoro-phenyl)-propynoic acid methyl ester

To a stirred solution of 1-(2,2-dibromo-vinyl)-3-fluorobenzene (23.8 g) in anhydrous THF (350 ml) cooled to −78° was added dropwise over 30 minutes, n-butyllithium (2.2 eq, 1.6M in hexanes). The mixture was stirred for a further 30 minutes at −78° before methyl chloroformate (11.6 g, 9.5 ml) was added and the resultant mixture allowed to warm to 0° for 1 hour before being diluted with 1:1 saturated aqueous sodium bicarbonate:ammonium chloride (100 ml) and extracted into ether (2×100 ml). The combined organic extract was washed with brine (25 ml), dried ($Na_2SO_4$) and evaporated to dryness to give the title compound as a brown oil (16.7 g, 100%). MH− 173

NMR (CDCl3) δ 7.4–7.1 (4H, m) 3.85 (3H, s, $CO_2Me$).

iv) 2-(3-Fluoro-phenyl)-6-trifluoromethyl-pyrazolo[1,5-a]pyridine-3-carboxylic acid methyl ester To a solution of (3-fluoro-phenyl)-propynoic acid methyl ester (1.75 g, 9.83 mmol) and 3-trifluoromethyl-pyridin-1-ylideneamine 2,4,6-trimethylphenylsulphonate (1.87 g, 5.17 mmol) in acetonitrile (15 ml) was added 1,8-diazabicyclo [5.4.0]undec-7-ene (1.47 ml) and the mixture heated to reflux for 30 minutes. The reaction was concentrated in vacuo, poured into water and extracted into ethyl acetate (2×50 ml). The combined organic phases were washed with water (20 ml), dried and purified by column chromatography with cyclohexane/ethyl acetate (20:1) as eluant. This gave the title compound as a white solid (448 mg, 26%).

1H NMR ($CDCl_3$) δ 8.9 (1H, s); 8.35 (1H, d, J 9 Hz); 7.60 (2H, 2×d, J 8 Hz); 7.55 (1H, d, J 10 Hz); 7.45 (1H, dt, J 8&6 Hz); 7.20 (1H, dt, J 8&2 Hz); 3.89 (3H, s).

v) 2-(3-Fluoro-phenyl)-6-trifluoromethyl-pyrazolo[1,5-a]pyridine-3-carboxylic acid To a suspension of 2-(3-fluoro-phenyl)-6-trifluoromethyl-pyrazolo[1,5-a]pyridine-3-carboxylic acid methyl ester (448 mg) in ethanol (10 ml) was added 2N sodium hydroxide and heated at reflux for 3 h. The cooled reaction mixture was acidified with 2N hydrochloric acid and the resulting solid isolated by filtration and dried in vacuo at 60° to give the title compound as an off-white solid (403 mg, 93%).

MH+=323

1H NMR (DMSO) δ 9.55 (1H, s); 8.3 (1H, d); 7.8 (1H, d); 7.65 (2H, 2×d); 7.55 (1H, m); 7.35 (1H, t).

vi) 3-Bromo-2-(3-fluoro-phenyl)-6-trifluoromethyl-pyrazolo[1,5-a]pyridine

To a solution of 2-(3-fluoro-phenyl)-6-trifluoromethyl-pyrazolo[1,5-a]pyridine-3-carboxylic acid (403 mg, 1.24 mmol) and $NaHCO_3$ (355 mg, 3.4 eq) in DMF (10 ml) was added NBS (1.1 eq, 244 mg) and the resulting solution stirred at rt for 1.5 h. The mixture was diluted with water and extracted with ethyl acetate (3×10 ml). The combined organic phases were washed with water (3×10 ml), dried and concentrated in vacuo to give the title compound as a brown solid (390 mg, 85%). MH+ 358/359

1H NMR ($CDCl_3$) 8.8 (1H, s); 7.9 (1H, d); 7.8 (1H, d); 7.65 (1H, d); 7.50 (1H, m); 7.35 (1H, d); 7.15 (1H, t).

vii) 4-[2-(3-Fluoro-phenyl)-6-trifluoromethyl-pyrazolo[1,5-a]pyridin-3-yl]benzenesulfonamide A mixture of 4-iodobenzenesulphonamide (651 mg); dipinacoldiborane (495 mg)[2]; potassium acetate (860 mg); and [1,1'-bis(diphenylphosphino)ferrocene]palladium(II) chloride complex:dichloromethane (1:1) (50 mg); in DMF (5 ml) was heated under nitrogen at 80° for 1.5 h. To the cooled reaction mixture was added 3-bromo-2-(3-fluoro-phenyl)-6-trifluoromethyl-pyrazolo[1,5-a]pyridine (330 mg, 0.919 mmol), 2N $Na_2CO_3$ (4 ml) and tetrakis(triphenylphosphine) palladium(0) (40 mg) and the mixture heated at reflux under nitrogen for 18 hours. The cooled reaction mixture was poured into water (30 ml) and the suspension extracted with ethyl acetate (3×20 ml). The organic extracts were combined, dried ($Na_2SO_4$) and concentrated in vacuo. The residue was purified by SPE chromatography eluting with a gradient of cyclohexane:ethyl acetate (100:0 to 0:100, 10% step). Trituration of the concentrated fractions containing product with diethyl ether gave the title compound as a white solid (139 mg, 35%). MH+ 436

1H ($CDCl_3$) 8.87 (1H, s); 8.0 (2H, d, J 8 Hz); 7.65 (1H, d, J 9 Hz); 7.50 (2H, d, J 8 Hz); 7.35 (4H, m); 7.10 (1H, t, J 8 Hz); 4.88 (2H, br s).

Ref 2: R. Miyaura et al J.Org.Chem., 1995, 60, 7508–7510

EXAMPLE 2

2-(3-Fluoro-phenyl)-3-(4-methanesulfonyl-phenyl)-6-trifluoromethyl-pyrazolo[1,5-a]pyridine To a solution of the 3-bromo-2-(3-fluoro-phenyl)-6-trifluoromethyl-pyrazolo[1,5-a]pyridine (50 mg, 0.139 mmol) in DMF (5 ml) was added 4-methanesulfonylphenylboronic acid (37 mg, 1.3 eq), ground potassium phosphate (83 mg) and tetrakis (triphenylphosphine)palladium(0) (10 mg) and the mixture heated to 90° for 18 h under $N_2$. The cooled mixture was poured into water (10 ml) and extracted into ethyl acetate (4×10 ml). The combined organic phases were washed sequentially with water, brine, 2N sodium hydroxide and brine, dried and concentrated in vacuo to give the title compound as an off-white solid (27 mg, 45%). MH+ 435

$_1$H NMR (CDCl$_3$) δ 8.9 (1H, s); 8.0 (2H, d, J 8 Hz); 7.65 (1H, d, J 9 Hz); 7.55 (2H, d, J 8 Hz); 7.25–7.4 (3H, m); 7.1 (1H, m); 3.15 (3H, s).

EXAMPLE 3

4-[2-(4-Ethoxy-phenyl)-6-trifluoromethyl-pyrazolo[1,5-a]pyridin-3-yl]benzenesulfonamide The process represented by Example 1(i)–(vii) was repeated, but substituting 4-ethoxybenzaldehyde for 3-fluorobenzaldehyde in step (ii). The title compound was obtained from 3-bromo-2-(4-ethoxy-phenyl)-6-trifluoromethyl-pyrazolo[1,5-a]pyridine in the manner described for Example 1(vii), as a white solid (127 mg, 44%).

MH+ 462

1H NMR (CDCl$_3$) δ 8.85 (1H, s); 7.95 (2H, d, J 8 Hz); 7.60 (1H, d, J 9 Hz); 7.52 (2H, d, 8 Hz); 7.47 (2H, d, J 8 Hz); 7.3 (1H, dd, J (&2 Hz); 6.9 (2H, d, J 9 Hz); 4.86 (2H, br s); 4.07 (2H, q, J 7 Hz); 1.45 (3H, t, J 7 Hz).

EXAMPLE 4

4-[2-(4-Fluoro-phenyl)-6-trifluoromethyl-pyrazolo[1,5-a]pyridin-3-yl]benzenesulfonamide The process represented by Example 1(i)–(vii), was repeated, but substituting 4-fluorobenzaldehyde for 3-fluorobenzaldehyde in step (ii). The title compound was obtained from 3-bromo-2-(4-fluoro-phenyl)-6-trifluoromethyl-pyrazolo[1,5-a]pyridine in the manner described for Example 1(vii), as a brown solid (240 mg, 70%).

MH+ 436

1H NMR (CDCl$_3$) δ 8.85 (1H, s); 8.0 (2H, d, J 8 Hz); 7.65 (1H, d, J 9 Hz); 7.5 (4H, m), 7.33 (1H, dd, J 9&1 Hz); 7.1 (2H, t, 8 Hz); 5.0 (2H, br s).

EXAMPLE 5

2-(4-Fluoro-phenyl)-3-(4-methanesulfonyl-phenyl)-6-trifluoromethyl-pyrazolo[1,5-a]pyridine By using 3-bromo-2-(4-fluoro-phenyl)-6-trifluoromethyl-pyrazolo[1,5-a]pyridine the title compound was obtained as a white solid (95 mg, 48%) in the manner described in Example 2.

MH+=435

1H NMR (CDCl$_3$) δ 8.87 (1H, s); 8.0 (2H, d, J 8 Hz); 7.67 (1H, d, J 9 Hz); 7.55 (4H, m); 7.35 (1H, dd, J 9&1 Hz); 7.1 (2H, t, J 9 Hz); 3.15 (3H, s).

EXAMPLE 6

4-(2-Phenyl-6-trifluoromethyl-pyrazolo[1,5-a]pyridin-3-yl)-benzenesulfonamide The process represented by Example 1(i)–(vii), was repeated, but substituting propynoic acid methyl ester (Lancaster) for 3-fluoro-phenyl)-propynoic acid methyl ester in step (iv). The title compound was obtained from 3-bromo-2-phenyl-6-trifluoromethyl-pyrazolo[1,5-a]pyridine in the manner described for Example 1(vii), as a white solid (140 mg, 43%). MH+ 418

1H NMR (CDCl$_3$) δ 8.85 (1H, s); 7.95 (2H, d, J 8 Hz); 7.65 (1H, d, J 9 Hz) 7.53 (3H, m); 7.4 (4H, m) 4.86 (2H, br s).

EXAMPLE 7

3-(4-Methanesulfonyl-phenyl)-2-phenyl-6-trifluoromethyl-pyrazolo[1,5-a]pyridine By using 3-bromo-2-phenyl-6-trifluoromethyl-pyrazolo[1,5-a]pyridine the title compound was obtained as an off-white solid (21 mg, 34%) in the manner described in Example 2. MH+ 417

1H NMR (CDCl$_3$) δ 8.87 (1H, s); 7.97 (2H, d, 8 Hz); 7.67 (1H, d, J 9 Hz); 7.55 (4H, m); 7.4 (4H, m); 3.15 (3H, s).

EXAMPLE 8

4-[2-(4-methyl-phenyl)-6-trifluoromethyl-pyrazolo[1,5-a]pyridin-3-yl]benzenesulfonamide The process represented by Example 1(i)–(vii), was repeated, but substituting 4-methylbenzaldehyde for 3-fluorobenzaldehyde in step (ii). The title compound was obtained from 3-bromo-2-(4-methyl-phenyl)-6-trifluoromethyl-pyrazolo[1,5-a]pyridine in the manner described for Example 1 (vii), as an off-white solid (168 mg, 36%). MH+ 432

1H CDCl$_3$ δ 8.85 (1H, s); 7.95 (2H, d, J 8 Hz); 7.63 (1H, d, J 9.3 Hz); 7.47 (2H, d, J 8 Hz); 7.44 (2H, d, J 8 Hz); 7.31 (1H, d, J 8 Hz); 7.18 (2H, d, J 8 Hz), 5.95 (2H, br s); 2.37 (3H, s).

EXAMPLE 9

N-Acetyl-4-[2-(3-fluorophenyl)-6-(trifluoromethyl)pyrazolo[1,5-a]pyridin-3-yl]benzenesulfonamide A mixture of 4-[2-(3-fluoro-phenyl)-6-trifluoromethyl-pyrazolo[1,5-a]pyridin-3-yl]benzenesulfonamide (0.2 g, 0.46 mmol) and acetyl chloride (Aldrich) (1 ml) in acetic acid (1 ml) was heated at 95° for 1 hr. The solvent was removed and the resulting oil was dissolved in ethyl acetate (30 ml), washed with M Na$_2$CO$_3$ (10 ml) and brine (10 ml). Drying (MgSO$_4$) and removal of solvent gave a white solid which was triturated with 40–60 petroleum ether, filtered and dried to give the title compound (0.17 g 77%). MH– 476

NMR (DMSO-d$_6$): δ 1.82 (3H, s) 7.25–7.35 (3H, m) 7.45–7.52 (2H, m) 7.48 (2H, d) 7.55 (1H, d) 7.84 (1H, d) 7.89 (2H, d) 9.48 (1H, s).

EXAMPLE 10

N-Acetyl-4-[2-(4-ethoxyphenyl)-6-(trifluoromethyl)pyrazolo[1,5-a]pyridin-3-yl]benzenesulfonamide By using 4-[2-(4-ethoxy-phenyl)-6-trifluoromethyl-pyrazolo[1,5-a]pyridin-3-yl]benzenesulfonamide (0.1 g 0.2 mmol), the title compound was obtained in the manner of Example 9 as a white solid (0.11 g 100%).

MH+: 504

NMR (CDCl₃): δ 1.44 (3H, t) 2.25 (3H, s) 4.07 (2H, q) 6.90 (2H, d) 7.32 (1H, d) 7.60 (2H, d) 7.65 (2H, d) 8.07 (2H, d) 8.27 (1H, br) 8.85 (1H, s).

EXAMPLE 11

N-Acetyl-4-[2-phenyl-6-(trifluoromethyl)pyrazolo[1,5-a]pyridin-3-yl]benzenesulfonamide By using 4-(2-phenyl-6-trifluoromethyl-pyrazolo[1,5-a]pyridin-3-yl)-benzenesulfonamide (0.1 g 0.2 mmol), the title compound was obtained in the manner of Example 9 as a light brown solid (0.11 g 100%).

MH+: 460

NMR (CDCl₃) δ 2.30 (3H, s) 7.34 (1H, s) 7.37–7.42 (3H, m) 7.51–7.56 (4H, m) 7.69 (1H, d) 8.07 (2H, d) 8.18 (1H, br) 8.88 (1H, s).

EXAMPLE 12

Sodium salt of N-acetyl-4-[2-(3-fluorophenyl)-6-(trifluoromethyl)pyrazolo[1,5-a]pyridin-3-yl]benzenesulfonamide To a solution of N-acetyl-4-[2-(3-fluorophenyl)-6-(trifluoromethyl)pyrazolo[1,5-a]pyridin-3-yl]benzenesulfonamide (0.087 g 0.2 mmol) in ethanol (5 ml) was added 2M sodium hydroxide (0.1 ml 0.2 mmol) and the mixture was allowed to stand at room temperature for 15 minutes. Removal of solvent gave a white solid which was triturated with diethyl ether, filtered and dried to give the title compound (0.08 g 80%).

EXAMPLE 13

4-[2-(3-Fluorophenyl)-6-(trifluoromethyl)pyrazolo[1,5-a]pyridin-3-yl]-N-(2-methoxyacetyl)benzenesulfonamide To a solution of 4-[2-(3-fluoro-phenyl)-6-trifluoromethyl-pyrazolo[1,5-a]pyridin-3-yl]-benzenesulfonamide (0.15 g 0.35 mmol) in dry THF (3 ml) was added N,N-(diisopropyl)aminomethylpolystyrene (Argonaut Technologies) (0.25 g 0.9 mmol), 4-dimethylaminopyridine (Aldrich) (0.03 g 0.25 mmol) and methoxyacetyl chloride (Aldrich) (0.09 g 0.8 mmol) and the mixture was shaken at room temperature for 18 hr. Tris-(2-aminoethyl)amine polystyrene (Argonaut Technologies) (0.5 g 1.7 mmol) was added and shaking continued for 6 hr. The resins were filtered, washed with dichloromethane (5 ml) and the solvents were removed. The residue was purified by SPE chromatography eluting with cyclohexane:ethyl acetate (5:1 then 2:1) to give the title compound as a white solid. (0.07 g, 40%).

MH+: 508

NMR (CDCl₃): δ 3.46 (3H, s) 3.94 (2H, s) 7.10 (1H, m) 7.25–7.38 (4H, m) 7.53 (2H, d) 7.68 (1H, d) 8.15 (2H, d) 8.86 (1H, s) 8.95 (1H, br).

EXAMPLE 14

4-[2-(3-Fluorophenyl)-6-(trifluoromethyl)pyrazolo[1,5-a]pyridin-3-yl]-N-propionylbenzenesulfonamide By using propionyl chloride (Aldrich) (0.092 g 1 mmol) the title compound was obtained in the manner of Example 13 as a white solid (0.11 g 63%).

MH+: 492

NMR (CDCl₃): δ 1.14 (3H, t) 2.36 (2H, q) 7.10 (1H, m) 7.25–7.40 (4H, m) 7.53 (2H, d) 7.68 (1H, d) 8.13 (2H, d) 8.20 (1H, br) 8.87 (1H, s).

EXAMPLE 15

4-[2-(3-Fluorophenyl)-6-(trifluoromethyl)pyrazolo[1,5-a]pyridin-3-yl]-N-isobutyrylbenzenesulfonamide By using isobutyryl chloride (Aldrich) (0.107 g 1 mmol) the title compound was obtained in the manner of Example 13 as a white solid (0.068 g 38%).

MH+: 506

NMR (CDCl₃): δ 1.15 (6H, d) 2.46 (1H, sept) 7.09 (1H, m) 7.25–7.40 (4H, m) 7.53 (2H, d) 7.68 (1H, d) 8.13 (2H, d) 8.45 (1H, br) 8.87 (1H, s).

EXAMPLE 16

N-Benzoyl-4-[2-(3-fluorophenyl)-6-(trifluoromethyl)pyrazolo[1,5-a]pyridin-3-yl]benzenesulfonamide By using benzoyl chloride (Aldrich) (0.21 g 1.5 mmol) the title compound was obtained in the manner of Example 13 as a white solid (0.07 g 37%). MH+: 540

NMR (CD₃OD): δ 6.98 (1H, m) 7.15–7.25 (3H, m) 7.27–7.35 (4H, m) 7.66 (1H, d) 7.40 (2H, d) 7.77 (2H, d) 7.99 (2H, d) 8.95 (1H, s).

EXAMPLE 17

Methyl 4-[({4-[2-(3-fluorophenyl)-6-(trifluoromethyl)pyrazolo[1,5-a]pyridin-3-yl]phenyl}sulfonyl)amino]-4-oxobutanoate By using 3-carbomethoxypropionyl chloride (Aldrich) (0.15 g 1 mmol) the title compound was obtained in the manner of Example 13 as a white solid (0.1 g 52%). MH+: 550

NMR (CDCl₃): δ 2.64 (4H, m) 3.66 (3H, s) 7.10 (1H, m) 7.23–7.37 (4H, m) 7.52 (2H, d) 7.68 (1H, d) 8.11 (2H, d) 8.70 (1H, br) 8.86 (1H, s).

EXAMPLE 18

4-[({4-[2-(3-Fluorophenyl)-6-(trifluoromethyl)pyrazolo[1,5-a]pyridin-3-yl]phenyl}sulfonyl)amino]-4-oxobutanoic acid A solution of methyl 4-[({4-[2-(3-fluorophenyl)-6-(trifluoromethyl)pyrazolo[1,5-a]pyridin-3-yl]phenyl}sulfonyl)amino]-4-oxobutanoate (0.1 g 0.1 8 mmol) in methanol (20 ml) was heated under reflux with 2M sodium hydroxide (0.45 ml 0.9 mmol) for 24 hr. The solvent was removed and the resulting solid was dissolved in water (20 ml) and the pH was adjusted to 2 with 2M hydrochloric acid. The liberated solid was extracted into ethyl acetate (3×20 ml) and the combined extracts were washed with water (20 ml) and brine (20 ml). Drying (MgSO₄) and removal of solvent gave the title compound as a white solid (0.09 g 92%). MH+: 536

NMR (CDCl₃): δ 2.62 (4H, m) 7.07 (1H, m) 7.22–7.37 (3H, m) 7.37 (1H, d) 7.53 (2H, d) 7.67 (1H, d) 8.10 (2H, d) 8.88 (1H, s) 9.04 (1H, br).

EXAMPLE 19

4-[2-(3-Fluorophenyl)-6-(trifluoromethyl)pyrazolo[1,5-a]pyridin-3-yl]-N-pentanoylbenzenesulfonamide To a solution of 4-[2-(3-fluoro-phenyl)-6-trifluoromethyl-pyrazolo[1,5-a]pyridin-3-yl]benzenesulfonamide (0.109 g 0.25 mmol) in chloroform (10 ml) was added diisopropyl-ethylamine (Aldrich) (100 μl), 4-dimethylaminopyridine (0.02 g 0.16 mmol) and valeryl chloride (Aldrich) (0.072 g 0.6 mmol) and the reaction was stirred at room temperature for 20 hr. It was washed with M $Na_2CO_3$ (5 ml), water (5 ml) and dried ($MgSO_4$). Removal of solvent gave a solid which was purified by SPE chromatography. Elution with cyclohexane:ethyl acetate (2:1) gave the title compound as a white solid (0.075 g 58%).

MH–: 518

NMR (Acetone-$d_6$): δ 0.77 (3H, t) 1.20 (2H, m) 1.45 (2H, m) 7.14 (1H, m) 7.23–7.42 (3H, m) 7.49 (1H, d) 7.58 (2H, d) 7.83 (1H, d) 8.04 (2H, d) 9.13 (1H, s).

EXAMPLE 20

2-[({4-[2-(3-Fluorophenyl)-6-(trifluoromethyl) pyrazolo[1,5-a]pyridin-3-yl]phenyl}sulfonyl)amino]-2-oxoethyl acetate By using 4-[2-(3-fluoro-phenyl)-6-trifluoromethyl-pyrazolo[1,5-a]pyridin-3-yl]benzenesulfonamide (0.15 g 0.35 mmol), diisopropylethylamine (Aldrich) (150 μl ), 4-dimethylaminopyridine (0.04 g 0.32 mmol) and acetoxyacetyl chloride (Aldrich) (0.109 g 0.8 mmol), the title compound was obtained in the manner of Example 19 as a white solid (0.14 g 75%).

MH+: 536

NMR ($CDCl_3$): δ 2.05 (3H, s) 4.55 (2H, s) 6.94 (1H, m) 7.10–7.30 (6H, m) 7.46 (1H, d) 7.97 (2H, d) 8.75 (1H, s).

EXAMPLE 21

N-Acetyl-4-[2-(4-fluorophenyl)-6-(trifluoromethyl) pyrazolo[1,5-a]pyridin-3-yl]benzenesulfonamide A solution of 4-[2-(4-fluoro-phenyl)-6-trifluoromethyl-pyrazolo[1,5-a]pyridin-3-yl]benzenesulphonamide (0.185 g 0.42 mmol), triethylamine (0.4 ml), 4-dimethylaminopyridine (0.024 g 0.18 mmol) and acetic anhydride (0.12 ml 1.2 mmol) in chloroform (10 ml) was stirred at room temperature for 4 hr. The reaction mixture was washed with 2M hydrochloric acid (10 ml), M $Na_2CO_3$ (5 ml) and water (10 ml). Drying ($MgSO_4$) and removal of solvent gave the title compound as a white solid (0.06 g 31%).

MH+ 478

NMR ($CDCl_3$): δ 2.05 (3H, s) 7.07 (2H, t) 7.34 (1H, d) 7.47 (2H, d) 7.55 (2H, m) 7.68 (1H, d) 8.05 (2H, d) 8.86 (1H, s).

EXAMPLE 22

N-(2-Chloroacetyl)-4-[2-(3-fluorophenyl)-6-(trifluoromethyl)pyrazolo[1,5-a]pyridin-3-yl] benzenesulfonamide By using 4-[2-(3-fluoro-phenyl)-6-trifluoromethyl-pyrazolo[1,5-a]pyridin-3-yl]benzenesulfonamide (0.7 g 1.6 mmol), triethylamine (1.6 ml), 4-dimethylaminopyridine (0.1 g 0.8 mmol) and chloroacetic anhydride (Aldrich) (0.825 g 4.8 mmol), the title compound was obtained the manner of Example 21 as a white solid (0.5 g 61%). MH–: 510, 512

NMR ($CDCl_3$): δ 4.08 (2H, s) 7.11 (1H, m) 7.30–7.40 (4H, m) 7.55 (2H, d) 7.68 (1H, d) 8.14 (2H, d) 8.87 (1H, s) 8.90 (1H, br).

EXAMPLE 23

N-[2-(Diethylamino)acetyl]-4-[2-(3-fluorophenyl)-6-(trifluoromethyl)pyrazolo[1,5-a]pyridin-3-yl] benzenesulfonamide A mixture of N-(2-chloroacetyl)-4-[2-(3-fluorophenyl)-6-(trifluoromethyl)pyrazolo[1,5-a]pyridin-3-yl] benzenesulfonamide (0.1 g 0.2 mmol), diethylamine (0.073 g 1 mmol) and sodium iodide (0.005 g 0.03 mmol) in dry THF (5 ml) was stirred at room temperature for 24 hr. The solvent was removed and the residues partitioned between ethyl acetate (10 ml) and water (10 ml). The organic layer was dried ($MgSO_4$), the solvent removed and the residues were purified by SPE chromatography using a cartridge containing an ion exchange sorbent that retains amino functionality. Elution with 5% acetic acid in methanol, ethyl acetate then 2M ammonia in methanol gave the title compound as a yellow solid (0.066 g 60%). MH+: 549

NMR ($CDCl_3$): δ 1.25 (6H, t) 3.12 (4H, q) 3.52 (2H, s) 7.05 (1H, m) 7.25–7.35 (4H, m) 7.44 (2H, d) 7.63 (1H, d) 8.08 (2H, d) 8.85 (1H, s).

Ref 3: e.g. an SCX containing cartridge (Isolute).

EXAMPLE 24

Methyl{4-[2-(3-fluorophenyl)-6-(trifluoromethyl) pyrazolo[1,5-a]pyridin-3-yl] phenyl}sulfonylcarbamate A Mixture of 4-[2-(3-fluoro-phenyl)-6-trifluoromethyl-pyrazolo[1,5-a]pyridin-3-yl]benzenesulfonamide (0.1 g 0.23 mmol), methyl chloroformate (Aldrich) (0.028 g 0.3 mmol) and potassium carbonate (0.07 g 0.05 mmol) were stirred and heated at reflux under nitrogen in acetone (10 ml) for 18 hr. Additional methyl chloroformate (0.028 g) and potassium carbonate (0.07 g) were added and heating continued for a further 24 hr. The reaction mixture was poured into water (100 ml) and extracted with ethyl acetate (3×50 ml). The combined extracts were washed with brine (30 ml), dried ($MgSO_4$) and the solvent removed. The residues were purified by SPE chromatography, elution with cyclohexane:ethyl acetate (3:1) gave the title compound as a white solid (0.03 g 26%). MH– 492

NMR ($CDCl_3$): δ 3.73 (3H, s) 7.10 (1H, m) 7.25–7.40 (4H, m) 7.52 (2H, d) 7.68 (1H, d) 8.06 (2H, d) 8.88 (1H, s).

EXAMPLE 25 tert-Butyl{4-[2-(3-fluorophenyl)-6-(trifluoromethyl) pyrazolo[1,5-a]pyridin-3-yl] phenyl}sulfonylcarbamate A Mixture of 4-[2-(3-fluoro-phenyl)-6-trifluoromethyl-pyrazolo[1,5-a]pyridin-3-yl]benzenesulfonamide (0.1 g 0.23 mmol), di-tert-butyl dicarbonate (Aldrich) (0.066 g 0.3 mmol) and 4-dimethylaminopyridine (0.004 g 0.03 mmol) were stirred in dry DCM (10 ml) containing triethylamine (100 μl) under nitrogen at room temperature for 2 hr. The reaction mixture was washed with 2M hydrochloric acid (10 ml), water (10 ml) and dried ($MgSO_4$). After removal of solvent the residues were purified by SPE chromatography, elution with cyclohexane:ethyl acetate (20:1) gave the title compound as a white solid (0.1 g 88%). MH+: 536

NMR ($CDCl_3$): δ 1.44 (9H, s) 7.10 (1H, m) 7.25–7.40 (4H, m) 7.53 (2H, d) 7.66 (1H, d) 8.06 (2H, d) 8.88 (1H, s).

Examples 26–35 were prepared according to procedures described hereinabove.

EXAMPLE 26

4-[6-chloro-2-(3-ethoxyphenyl)pyrazolo[1,5-a] pyridin-3-yl]benzenesulfonamide

MH–, 426.

EXAMPLE 27

6-chloro-2-(3-ethoxyphenyl)-3-[4-(methylsulfonyl) phenyl]pyrazolo[1,5-a]pyridine

MH+, 427.

EXAMPLE 28

4-[6-methyl-2-phenyl-pyrazolo[1,5-a]pyridin-3-yl]benzenesulfonamide

MH+, 364.

EXAMPLE 29

4-[2-(3-fluorophenyl)-6-methyl-pyrazolo[1,5-a]pyridin-3-yl]benzenesulfonamide

MH+, 382.

EXAMPLE 30

4-[2-(3-ethoxyphenyl)-6-methyl-pyrazolo[1,5-a]pyridin-3-yl]benzenesulfonamide

MH+, 408.

EXAMPLE 31

4-[2-(4-ethoxyphenyl)-6-methyl-pyrazolo[1,5-a]pyridin-3-yl]benzenesulfonamide

MH+, 408.

EXAMPLE 32

6-methyl-2-phenyl-3-[4-(methylsulfonyl)phenyl]pyrazolo[1,5-a]pyridine

MH+, 363.

EXAMPLE 33

2-(3-fluorophenyl)-6-methyl-3-[4-(methylsulfonyl)phenyl]pyrazolo[1,5-a]pyridine

MH+, 381.

EXAMPLE 34

2-(3-ethoxyphenyl)-6-methyl-3-[4-(methylsulfonyl)phenyl]pyrazolo[1,5-a]pyridine

MH+, 407.

EXAMPLE 35

2-(4-ethoxyphenyl)-6-methyl-3-[4-(methylsulfonyl)phenyl]pyrazolo[1,5-a]pyridine

MH+, 407.

EXAMPLE 36

Tablets

| | | | |
|---|---|---|---|
| a) | Compound of the invention | | 5.0 mg |
| | Lactose | | 95.0 mg |
| | Microcrystalline Cellulose | | 90.0 mg |
| | Cross-linked polyvinylpyrrolidone | | 8.0 mg |
| | Magnesium Stearate | | 2.0 mg |
| | Compression weight | | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| | | | |
|---|---|---|---|
| b) | Compound of the invention | | 5.0 mg |
| | Lactose | | 165.0 mg |
| | Pregelatinised Starch | | 20.0 mg |
| | Cross-linked polyvinylpyrrolidone | | 8.0 mg |
| | Magnesium Stearate | | 2.0 mg |
| | Compression weight | | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 37

Capsules

| | | | |
|---|---|---|---|
| a) | Compound of the invention | | 5.0 mg |
| | Lactose | | 193.0 mg |
| | Magnesium Stearate | | 2.0 mg |
| | Fill weight | | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| | | | |
|---|---|---|---|
| b) | Compound of the invention | | 5.0 mg |
| | Lactose | | 177.0 mg |
| | Polyvinylpyrrolidone | | 8.0 mg |
| | Cross-linked polyvinylpyrrolidone | | 8.0 mg |
| | Magnesium Stearate | | 2.0 mg |
| | Fill weight | | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

EXAMPLE 38

Syrup

| | | | |
|---|---|---|---|
| a) | Compound of the invention | | 5.0 mg |
| | Hydroxypropyl Methylcellulose | | 45.0 mg |
| | Propyl Hydroxybenzoate | | 1.5 mg |
| | Butyl Hydroxybenzoate | | 0.75 mg |
| | Saccharin Sodium | | 5.0 mg |
| | Sorbitol Solution | | 1.0 ml |
| | Suitable Buffers | | qs |

-continued

| | |
|---|---|
| Suitable flavours | qs |
| Purified Water to | 10.0 ml |

The hydroxypropyl methylcellulose is dispersed in a portion of hot purified water together with the hydroxybenzoates and the solution is allowed to cool to ambient temperature. The saccharin, sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

EXAMPLE 39

Injection Formulation

| | % w/v |
|---|---|
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 10 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.5, 2.0 and 5% w/v of the compound of the invention, so as to provide respectively 5, 20 and 50 mg/ml of the compound of the invention.

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 cm$^2$ flasks in which they were grown, onto 24-well cell culture plates using the following procedure. The incubation medium (Dulbecco's modified eagles medium (DMEM) supplemented with heat-inactivated foetal calf serum (10%v/v), penicillin (100 IU/ml), streptomycin (100 μg/ml) and geneticin (600 μg/ml)) was removed from a flask of confluent cells (1 flask at confluency contains approximately $1 \times 10^7$ cells). 10 ml of phosphate buffered saline (PBS) was added to the flask to wash the cells. Having discarded the PBS, cells were then rinsed in 10 ml trypsin for 20 seconds, after which the trypsin was removed and the flask placed in an incubator (37°) for 1–2 minutes until cells became detached from the flask. The flask was then removed from the incubator and cells resuspended in 10 ml of fresh incubation medium. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% $CO_2$) overnight. If more than 1 flask of cells were required, the cells from flasks were combined before being dispensed into the 24-well plates.

Following the overnight incubation, the incubation medium was completely removed from the 24-well cell culture plates and replaced with 250 μl fresh DMEM (37° C.). The test compounds were made up to 250× the required test concentration in DMSO and were added to the wells in a volume of 1 μl. Plates were then mixed gently by swirling and then placed in an incubator for 1 hour (37° C., 95% air/5% $CO_2$). Following the incubation period, 10 μl of arachidonic acid (750 μM) was added to each well to give a final arachidonic acid concentration of 30 μM. Plates were then incubated for a further 15 minutes, after which the incubation medium was removed from each well of the plates and stored −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values. The following $IC_{50}$ values for inhibition of COX-2 and COX-1 were obtained for compounds of the invention:

| Example No. | COX-2: $IC_{50}$ (nM) | COX-1: $IC_{50}$ (nM) |
|---|---|---|
| 1(vii) | 34 | >100,000 |
| 2 | 548 | >100,000 |
| 3 | 34 | 32,200 |
| 4 | 34 | >100,000 |
| 5 | 26 | >100,000 |
| 6 | 31 | 26350 |
| 7 | 30 | >100,000 |

What is claimed is:

1. A compound of formula (I)

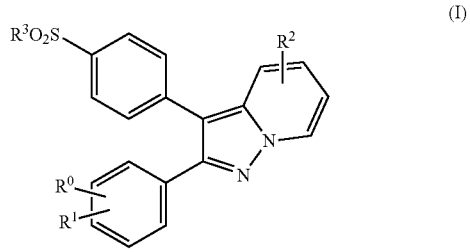

or a pharmaceutically acceptable derivative thereof wherein
$R^0$ and $R^1$ are independently selected from the group consisting of H, halogen, $C_{1-6}$alkyl, $C_{1-6}$alkoxy, and $C_{1-6}$alkoxy substituted by one or more fluorine atoms;
$R^2$ is selected from the group consisting of H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, C(O)H, C(O)$C_{1-6}$alkyl, $C_{1-6}$alkylsulphonyl, and $C_{1-6}$alkoxy substituted by one or more fluorine atoms; and
$R^3$ is $C_{1-6}$alkyl or $NH_2$.

2. A compound as claimed in claim 1 wherein $R^0$ and $R^1$ are independently selected from the group consisting of H, halogen, $C_{1-6}$alkyl, and $C_{1-6}$alkoxy; $R^2$ is $C_{1-3}$alkyl substituted by one or more fluorine atoms; and $R^3$ is $C_{1-3}$alkyl or $NH_2$.

3. A compound as claimed in claim 1 wherein $R^0$ and $R^1$ are independently selected from the group consisting of H, F, Cl, $C_{1-3}$alkyl, and $C_{1-3}$alkoxy; $R^2$ is $C_{1-3}$alkyl substituted by one or more fluorine atoms; and $R^3$ is methyl or $NH_2$.

4. A compound as claimed in claim 1 wherein $R^0$ is selected from the group consisting of F, Cl, $C_{1-3}$alkyl and $C_{1-3}$alkoxy; $R^1$ is H; $R^2$ is $C_{1-3}$alkyl substituted by one or more fluorine atoms; and $R^3$ is methyl or $NH_2$.

5. A compound as claimed in claim 1 wherein $R^0$ is at the 3- or 4-position of the phenyl ring; and $R^2$ is at the 6-position of the pyridine ring.

6. A compound selected from the group consisting of:
  4-[2-(3-fluoro-phenyl)-6-trifluoromethyl-pyrazolo[1,5-a] pyridin-3-yl]benzenesulfonamide;
  2-(3-fluoro-phenyl)-3-(4-methanesulfonyl-phenyl)-6-trifluoromethyl-pyrazolo[1,5-a]pyridine;
  4-[2-(4-ethoxy-phenyl-6-trifluoromethyl-pyrazolo[1,5-a] pyridin-3-yl]benzenesulfonamide;
  4-[2-(4-fluoro-phenyl)-6-trifluoromethyl-pyrazolo[1,5-a] pyridin-3-yl]benzenesulfonamide;
  2-(4-fluoro-phenyl)-3-(4-methanesulfonyl-phenyl)-6-trifluoromethyl-pyrazolo[1,5-a]pyridine;
  4-(2-phenyl-6-trifluoromethyl-pyrazolo[1,5-a]pyridin-3-yl)-benzenesulfonamide;
  3-(4-methanesulfonyl-phenyl)-2-phenyl-6-trifluoromethyl-pyrazolo[1,5-a]pyridine;
  4-[2-(4-methyl-phenyl)-6-trifluoromethyl-pyrazolo[1,5-a]pyridin-3-yl]benzenesulfonamide;
  or a pharmaceutically acceptable derivative thereof.

7. A compound selected from the group consisting of:
  N-acetyl-4-[2-(3-fluorophenyl)-6-(trifluoromethyl) pyrazolo[1,5-a]pyridin-3-yl]benzenesulfonamide;
  N-acetyl-4-[2-(4-ethoxyphenyl)-6-(trifluoromethyl) pyrazolo[1,5-a]pyridin-3-yl]benzenesulfonamide;
  N-acetyl-4-[2-phenyl-6-(trifluoromethyl)pyrazolo[1,5-a] pyridin-3-yl]benzenesulfonamide;
  sodium salt of N-acetyl-4-[2-(3-fluorophenyl)-6-(trifluoromethyl)pyrazolo[1,5-a]pyridin-3-yl] benzenesulfonamide;
  4-[2-(3-fluorophenyl)-6-(trifluoromethyl)pyrazolo[1,5-a] pyridin-3-yl]-N-(2-methoxyacetyl) benzenesufonamide;
  4-[2-(3-fluorophenyl)-6-(trifluoromethyl)pyrazolo[1,5-a] pyridin-3-yl]-N-propionylbenzenesulfonamide;
  4-[2-(3-fluorophenyl)-6-(trifluoromethyl)pyrazolo[1,5-a] pyridin-3-yl]-N-isobutyrylbenzenesulfonamide;
  N-benzoyl-4-[2-(3-fluorophenyl)-6-(trifluoromethyl) pyrazolo[1,5-a]pyridin-3-yl]benzenesulfonamide;
  methyl 4-[({4-[2-(3-fluorophenyl)-6-(trifluoromethyl) pyrazolo[1,5-a]pyridin-3-yl]phenyl}sulfonyl)amino]-4-oxobutanoate;
  4-[({4-[2-(3-fluorophenyl)-6-(trifluoromethyl)pyrazolo [1,5-a]pyridin-3-yl]phenyl}sulfonyl)amino]-4-oxobutanoic acid;
  4-[2-(3-fluorophenyl)-6-(trifluoromethyl)pyrazolo[1,5-a] pyridin-3-yl]-N-pentanoylbenzenesulfonamide;
  2-[({4-[2-(3-fluorophenyl)-6-(trifluoromethyl)pyrazolo [1,5-a]pyridin-3-yl]phenyl}sulfonyl)amino]-2-oxoethyl acetate;
  N-acetyl-4-[2-(4-fluorophenyl)-6-(trifluoromethyl) pyrazolo[1,5-a]pyridin-3-yl]benzenesulfonamide;
  N-(2-chloroacetyl)-4-[2-(3-fluorophenyl)-6-(trifluoromethyl)pyrazolo[1,5-a]pyridin-3-yl] benzenesulfonamide;
  N-[2-(diethylamino)acetyl]-4-[2-(3-fluorophenyl)-6-(trifluoromethyl)pyrazolo[1,5-a]pyridin-3-yl] benzenesulfonamide;
  methyl{4-[2-(3-fluorophenyl)-6-(trifluoromethyl) pyrazolo[1,5-a]pyridin-3-yl] phenyl}sulfonylcarbamate; and
  tert-butyl{4-[2-(3-fluorophenyl)-6-(trifluoromethyl) pyrazolo[1,5-a]pyridin-3-yl] phenyl}sulfonylcarbamate.

8. A compound selected from the group consisting of:
  4-[6-chloro-2-(3-ethoxyphenyl)pyrazolo[1,5-a]pyridin-3-yl]benzenesulfonamide;
  6-chloro-2-(3-ethoxyphenyl)-3-[4-(methylsulfonyl) phenyl]pyrazolo[1,5-a]pyridine;
  4-[6-methyl-2-phenyl-pyrazolo[1,5-a]pyridin-3-yl] benzenesulfonamide;
  4-[2-(3-fluorophenyl)-6-methyl-pyrazolo[1,5-a]pyridin-3-yl]benzenesulfonamide;
  4-[2-(3-ethoxyphenyl)-6-methyl-pyrazolo[1,5-a]pyridin-3-yl]benzenesulfonamide;
  4-[2-(4-ethoxyphenyl)-6-methyl-pyrazolo[1,5-a]pyridin-3-yl]benzenesulfonamide;
  6-methyl-2-phenyl-3-[4-(methylsulfonyl)phenyl] pyrazolo[1,5-a]pyridine;
  2-(3-fluorophenyl)-6-methyl-3-[4-(methylsulfonyl) phenyl]pyrazolo[1,5-a]pyridine;
  2-(3-ethoxyphenyl)-6-methyl-3-[4-(methylsulfonyl) phenyl]pyrazolo[1,5-a]pyridine;
  2-(4-ethoxyphenyl)-6-methyl-3-[4-(methylsulfonyl) phenyl]pyrazolo[1,5-a]pyridine;
  or a pharmaceutically acceptable derivative thereof.

9. A process for the preparation of a compound as claimed in claim 1, said process comprising the steps of:
  (A) reacting a compound of formula (II)

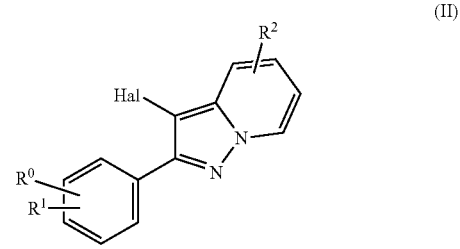

(II)

or a protected derivative thereof, with a compound of formula (III)

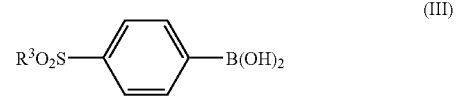

(III)

or a protected derivative thereof to prepare a compound of formula (I); and
  (B) optionally converting the compound of formula (I) to a pharmaceutically acceptable derivative thereof.

10. A pharmaceutical composition comprising a compound as claimed in claim 1 in admixture with one or more physiologically acceptable carriers or excipients.

11. A method of treating an animal subject suffering from an inflammatory disorder, which method comprises administering to said subject an effective amount of a compound claimed In claim 1.

12. The compound according to claim 1, wherein $R^0$ is selected from the group consisting of F, Cl, methyl and ethoxy; $R^1$ is H; $R^2$ is trifluoromethyl; and $R^3$ is methyl or $NH_2$.

13. A process for the preparation of a compound as claimed in claim 1, said process comprising the steps of:

(A) where $R^3$ represents $C_{1-4}$alkyl, reacting a compound of formula (IV)

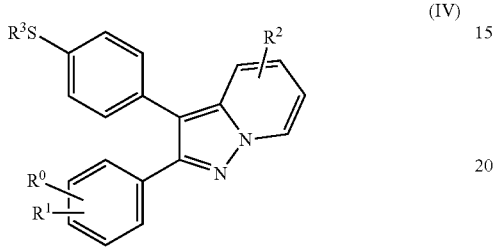

(IV)

or a protected derivative thereof with an oxidising agent to prepare a compound of formula (I); and (B) optionally converting the compound of formula (I) to a pharmaceutically acceptable derivative thereof.

14. A process for the preparation of a compound as claimed in claim 1, said process comprising the steps of:

(A) where $R^2$ is $C_{1-6}$alkylsulphonyl, oxidising a compound of formula (V)

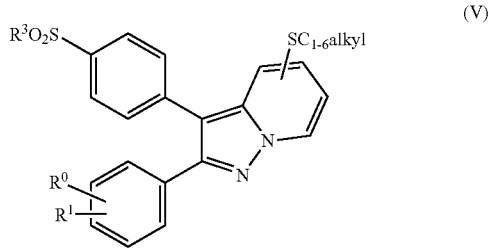

(V)

or a protected derivative thereof to prepare a compound of formula (I); and (B) optionally converting the compound of formula (I) to a pharmaceutically acceptable derivative thereof.

15. A process for the preparation of a compound as claimed in claim 1, said process comprising the steps of:

(A) where $R^2$ is $C_{1-6}$alkoxy substituted by one or more fluorine atoms, reacting a alcohol of formula (VI)

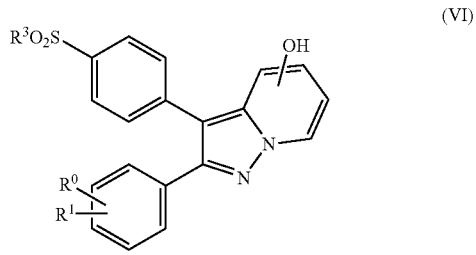

(VI)

or a protected derivative thereof with a halofluoroalkane to prepare a compound of formula (I); and (B) optionally converting the compound of formula (I) to a pharmaceutically acceptable derivative thereof.

16. A process for the preparation of a compound as claimed in claim 1, said process comprising the steps of:

(A) where $R^3$ is $NH_2$, reacting a compound of formula (X)

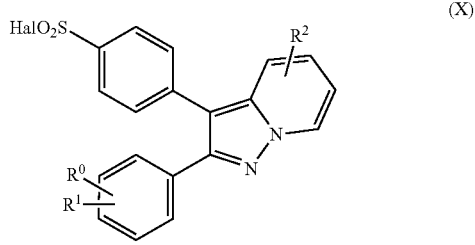

(X)

with a source of ammonia under conventional conditions to prepare a compound of formula (I); and (B) optionally converting the compound of formula (I) to a pharmaceutically acceptable derivative thereof.

17. A process for the preparation of a compound as claimed in claim 1, said process comprising the steps of:

(A) interconverting a compound of formula (I) into another compound of formula (I); and (B) optionally converting the compound of formula (I) to a pharmaceutically acceptable derivative thereof.

18. A process for the preparation of a compound as claimed in claim 1, said process comprising the steps of:

(A) deprotecting a protected derivative of compound of formula (I); and (B) optionally converting the compound of formula (I) to a pharmaceutically acceptable derivative thereof.

19. A method for the prophylaxis or treatment of a human subject suffering from an inflammatory disorder, which method comprises administering to said subject an effective amount of a compound as claimed in claim 1.

20. A method for the prophylaxis or treatment of a human subject suffering from a condition or disease selected from the group consisting of pain, fever and inflammation, said method comprising administering an effective amount of a compound as claimed in claim 1.

21. The method according to claim 20, wherein said condition or disease is selected from the group consisting of rheumatic fever, symptoms associated with influenza or other viral infections, lower back pain, neck pain, headache, toothache, sprains, strains, myositis, neuropathic pain, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, injuries arising from surgical procedures and injuries arising from dental procedures.

22. A method for the prophylaxis or treatment of a human subject suffering from pain, said method comprising administering an effective amount of a compound of formula (I) as claimed in claim 1.

23. A method for the prophylaxis or treatment of a human subject suffering from arthritis, said method comprising administering an effective amount of a compound of formula (I) as claimed in claim 1.

24. A method for the prophylaxis and treatment of a human subject suffering from a condition involving inflammatory processes, said method comprising administering an effective amount of a compound of formula (I) as claimed in claim 1, wherein said condition involving inflammatory processes are selected from the group consisting of asthma, allergic rhinitis, respiratory distress syndrome, inflammatory bowel disease, Crohn's disease, gastritis, irritable bowel syndrome, ulcerative colitis, vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

25. A method for the prophylaxis or treatment of a human subject suffering from a cognitive disorder, said method comprising administering an effective amount of a compound of formula (I) as claimed in claim 1.

26. The method of claim 25 wherein said cognitive disorder is selected from the group consisting of degenerative dementia, senile dementia, Alzheimer's disease, Pick's disease, Huntington's chorea, Parkinson's disease, Creutzfeldt-Jakob disease, vascular dementia, multi-infarct dementia, dementia associated with intracranial space occupying lesions, trauma, infections, metabolism, toxins, anoxia, and vitamin deficiency; and mild cognitive impairment associated with aging.

27. The method of claim 25, wherein said cognitive disorder is dementia.

28. The method of claim 25, wherein said cognitive disorder is Alzheimer's disease.

29. 4-[2-(3-fluoro-phenyl)-6-trifluoromethyl-pyrazolo[1,5-a]pyridin-3-yl]benzenesulfonamide.

* * * * *

UNITED STATES PATENT AND TRADEMARK OFFICE
CERTIFICATE OF CORRECTION

PATENT NO. : 7,223,772 B1 Page 1 of 17
APPLICATION NO. : 09/830836
DATED : May 29, 2007
INVENTOR(S) : Campbell et al.

It is certified that error appears in the above-identified patent and that said Letters Patent is hereby corrected as shown below:

Please delete the Title page and Column 1 line 1 through Column 30 line 13 and insert the Title page and Column 1 line 1 through Column 30 line 27 as attached.

Signed and Sealed this

Twenty-seventh Day of July, 2010

David J. Kappos
*Director of the United States Patent and Trademark Office*

(12) United States Patent
Campbell et al.

(10) Patent No.: US 7,223,772 B1
(45) Date of Patent: May 29, 2007

(54) PYRAZOLOPYRIDINE DERIVATIVES AS SELECTIVE COX-2 INHIBITORS

(75) Inventors: Ian Baxter Campbell, Broom (GB); Alan Naylor, Royston (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/830,836

(22) PCT Filed: Nov. 1, 1999

(86) PCT No.: PCT/EP99/08186
§ 371 (c)(1),
(2), (4) Date: May 1, 2001

(87) PCT Pub. No.: WO00/26216
PCT Pub. Date: May 11, 2000

(30) Foreign Application Priority Data

| Nov. 3, 1998 | (GB) | 9824062 |
|---|---|---|
| Sep. 3, 1999 | (GB) | 9920909 |

(51) Int. Cl.
*A61K 31/415* (2006.01)
*A61K 31/44* (2006.01)
*C07D 231/56* (2006.01)
*C07D 471/02* (2006.01)

(52) U.S. Cl. .............. 514/300; 548/362.5; 546/119; 514/406

(58) Field of Classification Search .......... 548/362.5; 514/406, 300; 546/119
See application file for complete search history.

(56) References Cited

U.S. PATENT DOCUMENTS

| 4,985,444 A | 1/1991 | Shiokawa et al. |
| 5,155,114 A | 10/1992 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |

FOREIGN PATENT DOCUMENTS

| EP | 0404 190 A1 | 12/1990 |
| EP | 0404 190 B1 | 12/1990 |
| EP | 0467248 B1 | 1/1992 |
| WO | 0364204 A1 | 4/1990 |
| WO | WO 9100092 | 1/1991 |
| WO | WO 9119497 | 12/1991 |
| WO | WO 95/00501 | 1/1995 |
| WO | WO96 06840 A | 3/1996 |
| WO | WO96 21667 A | 7/1996 |
| WO | WO96 31509 A | 10/1996 |
| WO | WO 9641625 | 12/1996 |
| WO | WO 9641626 | 12/1996 |
| WO | WO 9641645 | 12/1996 |
| WO | WO99 12930 A | 3/1999 |
| WO | WO 0114375 | 3/2001 |

OTHER PUBLICATIONS

Kakehi, et. al, "Preparation of New Nitrogen-Bridged Heterocycles. 18. Facile Formations of 3-Arylpyrazolo [1,5-a] pyridines and 1-Arylindolizines", Bull. Chem. Soc. Jpn. 61, 2055-2061, 1988.*
Akahane, A. et al., "Discovery of 6-Oxo-3-(2-phenylpyrazolo [1,5-a] pyridin-3-yl)-1(6H)-pyridazinebutanoic Acid (FK 838): A Novel Non-Xanthine Adenosine $A_1$ Receptor Antagonist with Potent Diuretic Activity", Journal of Medicinal Chemistry, vol. 42, No. 5, 11 Mar. 1999, pp. 779–784.
Talley, John J., Progress in Medicinal Chemistry, vol. 36, (1999), pp. 201–234.
Vane, John, Nature, vol. 367: (1994) pp. 215–216.
Therien, M., et al: "Synthesis and Biological Evaluation of 5,6-diarylimidazo' 2.1-b!thiaz ole as Selective COX-2 Inhibitors", Bioorganic & Medicinal Chemistry Letters, GB, Oxford, vol. 7, No. 1, Jan. 7, 1997, pp. 47–52.
Roy, P., et al: "A New Series of Selective COX-2 Inhibitors: 5,6-diarylthiazolo'3,2-b!'1,2,4!triazoles", Bioorganic & Medicinal Chemistry Letters, GB, Oxford, vol. 7, No. 1, Jan. 7, 1997, pp. 57–62.
Talley, J. J.: "Selective Inhibitors of Cyclooxygenase-2", Expert Opinion on Therapeutic Patents, GB, Ashley Publications, vol. 7, No. 1, Jan. 1, 1997, pp. 55–62.
Carter, J. S.: "Recently Reported Inhibitors of Cyclooxygenase-2", Expert Opinion on Therapeutic Patents, GB, Ashley Publications, vol. 8, No. 1, Jan. 1, 1998, pp. 21–29.

* cited by examiner

*Primary Examiner*—Alan L. Rotman
*Assistant Examiner*—Binta Robinson
(74) *Attorney, Agent, or Firm*—J. Scott Young

(57) ABSTRACT

The invention provides the compounds of formula (I)

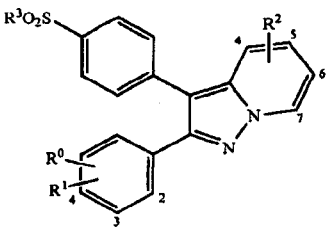

(I)

and pharmaceutically acceptable derivatives thereof wherein:

$R^0$ and $R^1$ are independently selected from the group consisting of H, halogen, $C_{1-6}$alkyl, $C_{1-6}$alkoxy, and $C_{1-6}$alkoxy substituted by one or more fluorine atoms;
$R^2$ is selected from the group consisting of H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, and $C_{1-6}$alkoxy substituted by one or more fluorine atoms; and
$R^3$ is $C_{1-6}$alkyl or $NH_2$.

Compounds of formula (I) are potent and selective inhibitors of COX-2 and are of use in the treatment of the pain, fever, inflammation of a variety of conditions and diseases.

26 Claims, No Drawings

PYRAZOLOPYRIDINE DERIVATIVES AS SELECTIVE COX-2 INHIBITORS

CROSS-REFERENCES TO RELATED APPLICATIONS

This application is a Rule 371 Application of PCT Application No. EP99/08186, filed 1 Nov. 1999, which claims priority to GB Application Serial No. 9824062.5, filed 3 Nov. 1998 and GB Application Serial No. 9920909.0, filed 3 Sep. 1999.

BACKGROUND OF THE INVENTION

This invention relates to pyrazolo[1,5-a]pyridine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is responsible for the important physiological functions such as maintenance of gastrointestinal integrity and renal blood flow. In contrast the inducible form, COX-2, is believed to be responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

DETAIL DESCRIPTION OF THE INVENTION

The invention thus provides the compounds of formula (I)

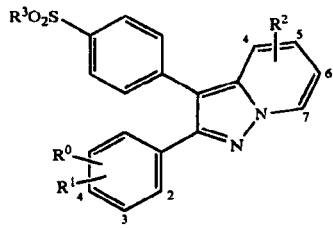

(I)

and pharmaceutically acceptable derivatives thereof in which:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms; and $R^3$ is $C_{1-6}$alkyl or $NH_2$.

By pharmaceutically acceptable derivative is meant any pharmaceutically acceptable salt, solvate, ester or amide, or salt or solvate of such ester or amide, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides.

Acylated benzenesulphonamide derivatives are of especial interest. Examples of such benzenesulphonamide derivatives include:

N-alkylcarbonylbenzenesulphonamides;
N-alkoxyalkylcarbonylbenzenesulphonamides;
N-alkoxycarbonylbenzenesulphonamides;
N-arylcarbonylbenzenesulphonamides;
N-alkoxycarbonylalkylcarbonylbenzenesulphonamides
N-carboxylalkylcarbonylbenzenesulphonamides
N-alkylcarbonyloxyalkylcarbonylbenzenesulphonamides;
N-alkylaminoalkylcarbonylbenzenesulphonamides; and
N-dialkylaminoalkylcarbonylbenzenesulphonamides.

With reference to such benzenesulphonamide derivatives, and by way of example only, alkyl may be $C_{1-6}$alkyl or $C_{1-6}$alkyl substituted by one or more halogen (e.g. chlorine) atoms; alkoxy may be $C_{1-6}$alkoxy or $C_{1-6}$alkoxy substituted by one or more halogen (e.g. chlorine) atoms; and aryl may be phenyl or substituted phenyl.

It will be appreciated by those skilled in the art that the pharmaceutically acceptable derivatives of the compounds of formula (I) may be derivatised at more than one position.

It will be further appreciated by those skilled in the art that benzenesulphonamide derivatives of formula (I) may be useful as intermediates in the preparation of compounds of formula (I), or as pharmaceutically acceptable derivatives of formula (I), or both.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts include: acid addition salts formed with inorganic or organic acids, preferably inorganic acids, e.g. hydrochlorides, hydrobromides and sulphates; and alkali metal salts, formed from addition of alkali metal bases, such as alkali metal hydroxides, e.g. sodium salts.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

In one aspect of the invention $R^0$ is at the 3- or 4-position of the phenyl ring, as defined in formula (I).

In another aspect of the invention $R^2$ is at the 6-position of the pyrazolopyridine ring, as defined in formula (I).

In another aspect of the invention $R^0$ and $R^1$ are independently H, halogen, $C_{1-6}$alkyl, or $C_{1-6}$alkoxy.

In another aspect of the invention $R^2$ is $C_{1-6}$alkyl substituted by one or more fluorine atoms.

In another aspect of the invention $R^3$ is $C_{1-3}$alkyl or $NH_2$.

Within the invention there is provided one group of compounds of formula (I) (group A) wherein: $R^0$ and $R^1$ are independently H, halogen, $C_{1-6}$alkyl, or $C_{1-6}$alkoxy; $R^2$ is $C_{1-3}$alkyl substituted by one or more fluorine atoms; and $R^3$ is $C_{1-3}$alkyl or $NH_2$.

Within group A, there is provided a further group of compounds (group A1) wherein: $R^0$ and $R^1$ are independently H, F, Cl, $C_{1-3}$alkyl (e.g. methyl), or $C_{1-3}$alkoxy (e.g. ethoxy); $R^2$ is $C_{1-3}$alkyl substituted by one or more fluorine atoms (e.g. trifluoromethyl); and $R^3$ is methyl or $NH_2$.

Within group A1, there is provided a further group of compounds (group A2) wherein: $R^0$ is F, Cl, or $C_{1-3}$alkyl (e.g. methyl) or $C_{1-3}$alkoxy (e.g. ethoxy); $R^1$ is H; $R^2$ is $C_{1-3}$alkyl substituted by one or more fluorine atoms (e.g. trifluoromethyl); and $R^3$ is methyl or $NH_2$.

Within groups A, A1 and A2 there are provided further groups of compounds wherein $R^0$ is at the 3- or 4-position of the phenyl ring, and $R^2$ is at the 6-position of the pyrazolopyridine ring, as defined in formula (I).

Within the invention there is provided another group of compounds of formula (I) (group B) wherein: $R^0$ and $R^1$ are independently H, halogen, $C_{1-6}$alkyl, or $C_{1-6}$alkoxy; $R^2$ is $C_{1-3}$alkyl; and $R^3$ is $C_{1-3}$alkyl or $NH_2$.

Within group B, there is provided a further group of compounds (group B1) wherein: $R^0$ and $R^1$ are independently H, F, or $C_{1-3}$alkoxy (e.g. ethoxy); $R^2$ is $C_{1-3}$alkyl (e.g. methyl); and $R^3$ is methyl or $NH_2$.

Within group B1, there is provided a further group of compounds (group B2) wherein: $R^0$ is H, F, or $C_{1-3}$alkoxy (e.g. ethoxy); $R^1$ is H; $R^2$ is $C_{1-3}$alkyl (e.g. methyl); and $R^3$ is methyl or $NH_2$.

Within groups B, B1 and B2 there are provided further groups of compounds wherein $R^0$ is at the 3- or 4-position of the phenyl ring, and $R^2$ is at the 6-position of the pyrazolopyridine ring, as defined in formula (I).

It is to be understood that the present invention encompasses all isomers of the compounds of formula (I) and their pharmaceutically acceptable derivatives, including all geometric, tautomeric and optical forms, and mixtures thereof (e.g. racemic mixtures).

In one aspect the invention provides the following compounds:
4-[2-(3-fluoro-phenyl)-6-trifluoromethyl-pyrazolo[1,5-a]pyridin-3-yl]benzenesulfonamide;
2-(3-fluoro-phenyl)-3-(4-methanesulfonyl-phenyl)-6-trifluoromethyl-pyrazolo[1,5-a]pyridine;
4-[2-(4-ethoxy-phenyl)-6-trifluoromethyl-pyrazolo[1,5-a]pyridin-3-yl]benzenesulfonamide;
4-[2-(4-fluoro-phenyl)-6-trifluoromethyl-pyrazolo[1,5-a]pyridin-3-yl]benzenesulfonamide;
2-(4-fluoro-phenyl)-3-(4-methanesulfonyl-phenyl)-6-trifluoromethyl-pyrazolo[1,5-a]pyridine;
4-(2-phenyl-6-trifluoromethyl-pyrazolo[1,5-a]pyridin-3-yl)-benzenesulfonamide;
3-(4-methanesulfonyl-phenyl)-2-phenyl-6-trifluoromethyl-pyrazolo[1,5-a]pyridine;
4-[2-(4-methyl-phenyl)-6-trifluoromethyl-pyrazolo[1,5-a]pyridin-3-yl]benzenesulfonamide;
and pharmaceutically acceptable derivatives thereof.

In another aspect the invention provides the following compounds:
N-acetyl-4-[2-(3-fluorophenyl)-6-(trifluoromethyl)pyrazolo[1,5-a]pyridin-3-yl]benzenesulfonamide;
N-acetyl-4-[2-(4-ethoxyphenyl)-6-(trifluoromethyl)pyrazolo[1,5-a]pyridin-3-yl]benzenesulfonamide;
N-acetyl-4-[2-phenyl-6-(trifluoromethyl)pyrazolo[1,5-a]pyridin-3-yl]benzenesulfonamide;
sodium salt of N-acetyl-4-[2-(3-fluorophenyl)-6-(trifluoromethyl)pyrazolo[1,5-a]pyridin-3-yl]benzenesulfonamide;
4-[2-(3-fluorophenyl)-6-(trifluoromethyl)pyrazolo[1,5-a]pyridin-3-yl]-N-(2-methoxyacetyl)benzenesulfonamide;
4-[2-(3-fluorophenyl)-6-(trifluoromethyl)pyrazolo[1,5-a]pyridin-3-yl]-N-propionylbenzenesulfonamide;
4-[2-(3-fluorophenyl)-6-(trifluoromethyl)pyrazolo[1,5-a]pyridin-3-yl]-N-isobutyrylbenzenesulfonamide;
N-benzoyl-4-[2-(3-fluorophenyl)-6-(trifluoromethyl)pyrazolo[1,5-a]pyridin-3-yl]benzenesulfonamide;
methyl 4-[({4-[2-(3-fluorophenyl)-6-(trifluoromethyl)pyrazolo[1,5-a]pyridin-3-yl]phenyl}sulfonyl)amino]-4-oxobutanoate;
4-[({4-[2-(3-fluorophenyl)-6-(trifluoromethyl)pyrazolo[1,5-a]pyridin-3-yl]phenyl}sulfonyl)amino]-4-oxobutanoic acid;
4-[2-(3-fluorophenyl)-6-(trifluoromethyl)pyrazolo[1,5-a]pyridin-3-yl]-N-pentanoylbenzenesulfonamide;
2-[({4-[2-(3-fluorophenyl)-6-(trifluoromethyl)pyrazolo[1,5-a]pyridin-3-yl]phenyl}sulfonyl)amino]-2-oxoethyl acetate;
N-acetyl-4-[2-(4-fluorophenyl)-6-(trifluoromethyl)pyrazolo[1,5-a]pyridin-3-yl]benzenesulfonamide;
N-(2-chloroacetyl)-4-[2-(3-fluorophenyl)-6-(trifluoromethyl)pyrazolo[1,5-a]pyridin-3-yl]benzenesulfonamide;
N-[2-(diethylamino)acetyl]-4-[2-(3-fluorophenyl)-6-(trifluoromethyl)pyrazolo[1,5-a]pyridin-3-yl]benzenesulfonamide;
methyl{4-[2-(3-fluorophenyl)-6-(trifluoromethyl)pyrazolo[1,5-a]pyridin-3-yl]phenyl}sulfonylcarbamate; and
tert-butyl{4-[2-(3-fluorophenyl)-6-(trifluoromethyl)pyrazolo[1,5-a]pyridin-3-yl]phenyl}sulfonylcarbamate.

In a further aspect the invention provides the following compounds:
4-[6-chloro-2-(3-ethoxyphenyl)pyrazolo[1,5-a]pyridin-3-yl]benzenesulfonamide;
6-chloro-2-(3-ethoxyphenyl)-3-[4-(methylsulfonyl)phenyl]pyrazolo[1,5-a]pyridine;
4-[6-methyl-2-phenyl-pyrazolo[1,5-a]pyridin-3-yl]benzenesulfonamide;
4-[2-(3-fluorophenyl)-6-methyl-pyrazolo[1,5-a]pyridin-3-yl]benzenesulfonamide;
4-[2-(3-ethoxyphenyl)-6-methyl-pyrazolo[1,5-a]pyridin-3-yl]benzenesulfonamide;
4-[2-(4-ethoxyphenyl)-6-methyl-pyrazolo[1,5-a]pyridin-3-yl]benzenesulfonamide;
6-methyl-2-phenyl-3-[4-(methylsulfonyl)phenyl]pyrazolo[1,5-a]pyridine;
2-(3-fluorophenyl)-6-methyl-3-[4-(methylsulfonyl)phenyl]pyrazolo[1,5-a]pyridine;
2-(3-ethoxyphenyl)-6-methyl-3-[4-(methylsulfonyl)phenyl]pyrazolo[1,5-a]pyridine;
2-(4-ethoxyphenyl)-6-methyl-3-[4-(methylsulfonyl)phenyl]pyrazolo[1,5-a]pyridine;
and pharmaceutically acceptable derivatives thereof.

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; neuropathic pain (e.g. neuralgia, such as post herpetic neuralgia, trigeminal neuralgia and sympathetically maintained pain); synovitis;

arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by selective inhibition of COX-2.

According to a further aspect of the invention, we provide a method of treating a human or animal subject suffering from a condition which is mediated by selective inhibition of COX-2 which comprises administering to said subject an effective amount of a compound of formula (I) or a pharmaceutically acceptable derivative.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by selective inhibition of COX-2.

According to another aspect of the invention, we provide the use of a compound of formula (I) or a pharmaceutically acceptable derivative thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include pain relievers such as a glycine antagonist, a sodium channel inhibitor (e.g. lamotrigine), a substance P antagonist (e.g. an $NK_1$ antagonist), acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor $\alpha$; an antibody therapy (e.g. a monoclonal antibody therapy); a stimulant, including caffeine; an $H_2$-antagonist, such as ranitidine; a proton pump inhibitor, such as omeprazole; an antacid, such as aluminium or magnesium hydroxide; an antiflatulent, such as simethicone; a decongestant, such as phenylephrine, phenylpropanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine.

It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below. In the discussion and formulae that follow $R^0$ to $R^3$ are as defined in formula (I) above unless otherwise stated; Hal is a halogen, such as Br or I; $X^-$ is a counterion, such as $I^-$; NBS is N-bromosuccinimide; NCS is N-chlorosuccinimide; DMF is N,N-dimethylformamide; and alkyl and halogen are as previously defined.

Thus according to a first process (A), compounds of formula (I) may be prepared by reacting a compound of formula (II)

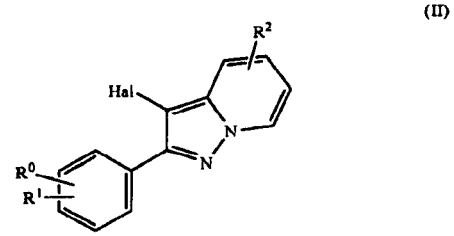

with a boronic acid of formula (III)

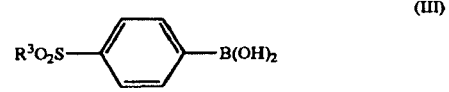

or a suitable derivative thereof in the presence of a suitable transition metal catalyst. Suitable derivatives of formula (III) include boronic acid esters, such as those described in R. Miyaura et al, J. Org. Chem., 1995, 60, 7508–7510. Conveniently, the reaction is carried out in a solvent, such as an ether (e.g. 1,2-dimethoxyethane); in the presence of a base, such as an inorganic base (e.g. sodium carbonate); and employing a palladium catalyst, such as tetrakis (triphenylphosphine)palladium(0).

According to a another process (B), compounds of formula (I) wherein $R^3$ is $C_{1-6}$alkyl may be prepared by oxidising a compound of formula (IV)

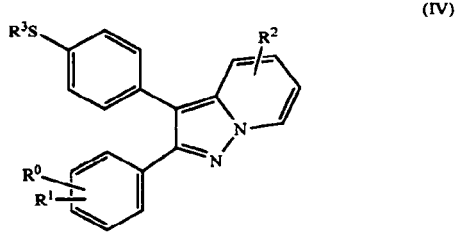

under conventional conditions. Conveniently the oxidation is effected using a monopersulfate compound, such as potassium peroxymonosulfate (known as Oxone™) and the reaction is carried out in a solvent, such as an aqueous alcohol, (e.g. aqueous methanol), and at between –78° C. and ambient temperature.

According to a another process (C), compounds of formula (I) wherein $R^2$ is $C_{1-6}$alkylsulphonyl may be prepared by oxidising a compound of formula (V)

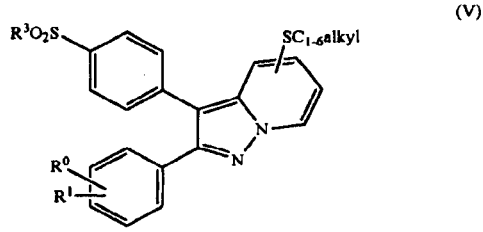

under conventional conditions. Conveniently the oxidation is effected in the manner described just above for process (B).

According to a another process (D), compounds of formula (I) wherein $R^2$ is $C_{1-6}$alkoxy substituted by one or more fluorine atoms may be prepared by reacting a phenol of formula (VI)

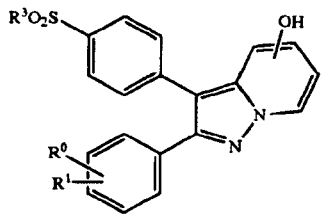

(VI)

with a halofluoroalkane under conventional conditions. Conveniently the reaction is effected in a solvent, such as a polar solvent (e.g. DMF), in the presence of a strong base, such as an inorganic hydride (e.g. sodium hydride), at about ambient temperature and using the appropriate bromofluoroalkane to give the desired compound of formula (I).

According to a another process (E), compounds of formula (I) wherein $R^3$ is $NH_2$ may be prepared by reacting a compound of formula (X)

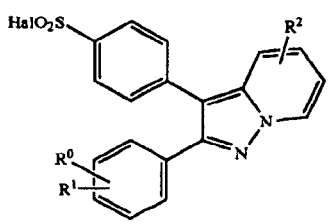

(X)

with a source of ammonia under conventional conditions. Conveniently the reaction is carried out in a solvent, such as an ester (e.g. ethyl acetate); at ambient or elevated temperature (e.g. ambient temperature); employing ammonium hydroxide as the source of ammonia and using a compound of formula (X) where Hal is Cl.

According to another process (F) compounds of formula (I) may be prepared by interconversion, utilising other compounds of formula (I) as precursors. The following procedures are illustrative of suitable interconversions.

Compounds of formula (I) wherein $R^2$ represents $C_{1-6}$alkyl substituted by one or more fluorine atoms may be prepared from the appropriate compound of formula (I) wherein $R^2$ is $C_{1-6}$hydroxyalkyl, C(O)H or C(O)$C_{1-6}$alkyl, by treatment with a suitable source of fluorine. Suitable sources of fluorine include, for example, (diethylamino) sulphur trifluoride. Conveniently the reaction is effected in the presence of a solvent, such as a halogenated hydrocarbon (e.g. dichloromethane), and at reduced temperature, such as $-78°$ C.

Compounds of formula (I) wherein $R^2$ represents C(O)H may be prepared from the corresponding compound of formula (I) wherein $R^2$ represents $CH_2OH$ by oxidation. Suitable oxidising agents include, for example, manganese (IV) oxide. Conveniently the oxidation is effected in the presence of a solvent, such as a halogenated hydrocarbon (e.g. chloroform), and at elevated temperature (e.g. under reflux).

Compounds of formula (I) wherein $R^2$ represents $C_{1-6}$hydroxyalkyl, and wherein the hydroxy group is attached to the carbon linked to the pyridine ring, may be prepared by reduction of the compound of formula (I)

wherein $R^2$ represents the corresponding aldehyde or ketone. Suitable reducing agents include hydride reducing agents, such as diisobutylaluminium hydride. Conveniently the reduction is effected in the presence of a solvent, such as a halogenated hydrocarbon (e.g. dichloromethane), and at reduced temperature, such as $-78°$ C.

As will be appreciated by those skilled in the art it may be necessary or desirable at any stage in the synthesis of compounds of formula (I) to protect one or more sensitive groups in the molecule so as to prevent undesirable side reactions.

Another process (G) for preparing compounds of formula (I) thus comprises deprotecting protected derivatives of compounds of formula (I).

The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Acylation of compounds of formula (I) wherein $R^3$ is $NH_2$ to provide corresponding acylated benzenesulphonamide derivatives may be carried out by conventional means, for example by employing conventional acylating agents such as those described in 'Advanced Organic Chemistry' by J March, fourth edition, (John Wiley and Sons, 1992), pp 417-424, incorporated herein by reference.

Compounds of formula (II) may be prepared by halogenating compounds of formula (VII)

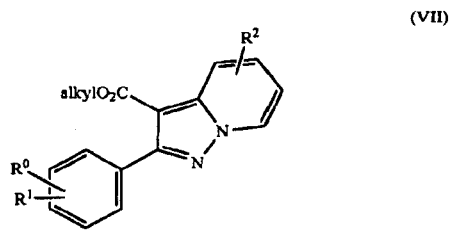

(VII)

by conventional means.

Thus esters of formula (VII) are first hydrolysed to their corresponding acids, for example by treatment with a strong base (e.g. sodium hydroxide), in the present of a solvent (e.g. ethanol) and at elevated temperature. The corresponding acid is then treated with a halogenating agent, conveniently at ambient temperature and in a solvent (e.g. chlorinated hydrocarbon), under which conditions the acid undergoes both halogenation and decarboxylation. Conveniently, the halogenating agent is a brominating agent, such as bromine in the presence of a strong acid (e.g. hydrobromic acid in acetic acid) or NBS, to yield the corresponding compound of formula (II) wherein Hal is bromine.

Esters of formula (VII) may be prepared by reacting a compound of formula (VIII)

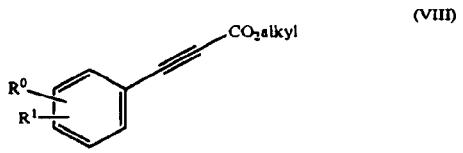

(VIII)

with an aminopyridinium complex of formula (IX)

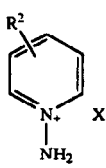
(IX)

under conventional conditions. Conveniently the reaction is effected in the presence of a base, such as potassium carbonate, a solvent, such as DMF and at ambient temperature.

Compounds of formula (II) may also be prepared by halogenating a compound of formula (XI)

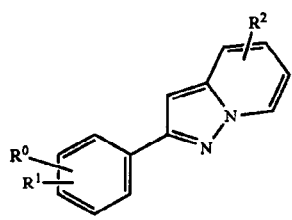
(XI)

by conventional means. Conveniently the halogenation is effected using a brominating agent (e.g. NBS), at ambient temperature and in a solvent (e.g. chlorinated hydrocarbon), to yield the corresponding compound of formula (II) wherein Hal is bromine. Compounds of formula (XI) may be prepared from an azirine of formula (XII)

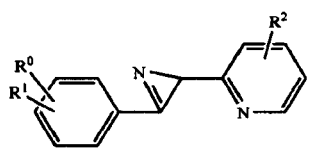
(XII)

by conventional means. Conveniently the reaction is effected in a solvent, such as an aromatic hydrocarbon (e.g. 1,2,4-trichlorobenzene) and at elevated temperature (e.g. under reflux).

Compounds of formula (XII) may be prepared from an oxime of formula (XIII)

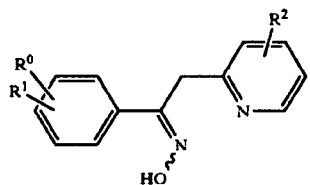
(XIII)

by conventional means. Conveniently the oxime is dissolved in a solvent such as a haloalkane (e.g. dichloromethane), treated a with a base, such as an amine (e.g. triethylamine), the mixture cooled to about 0° C. and treated with an anhydride (e.g. trifluoroacetic anhydride), and the mixture then allowed to warm to ambient temperature.

Compounds of formula (XIII) may be prepared from a ketone of formula (XIV)

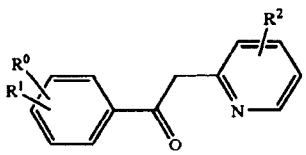
(XIV)

by conventional means. Conveviently the reaction is effected with hydroxylamine or a salt thereof (e.g. hydroxylamine hydrochloride), in a solvent such as an alcohol (e.g. methanol) and at ambient temperature.

Compounds of formula (XIV) may be prepared by reacting a compound of formula (XV)

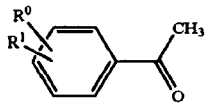
(XV)

with a compound of formula (XVI)

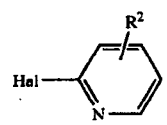
(XVI)

under conventional conditions. Conveviently the compound of formula (XVI) is a chloro derivative and the reaction is effected in the presence of a strong base, such as an inorganic hydride (e.g. sodium hydride) and at about ambient temperature.

Boronic acids of formula (III) are either known compounds or may be prepared by literature methods such as those described in, for example, EPA publication No. 533268.

Compounds of formula (X) may be prepared by sulphonylating a compound of formula (XVII)

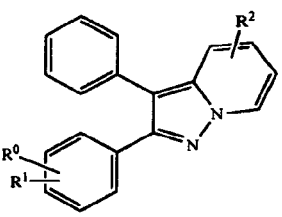
(XVII)

under conventional conditions. Conveniently the sulphonylation is effected using sulphonic acid or a derivative thereof, such as a halosulphonic acid (e.g. chlorosulphonic acid); in the presence of a solvent, such as a halogenated alkane (e.g. dichloromethane); and at between −78° C. and ambient temperature (e.g. −70° C.).

Compounds of formulae (IV), (V) and (VI) and (XVII) may be prepared by methods analogous to those described for the preparation of the corresponding compounds of formula (I).

Compounds of formulae (VIII), (IX), (XV), (XVI) are either known compounds or may be prepared by literature methods such as those described in, for example:

D H Wadsworth et al, J Org Chem, (1987), 52(16), 3662–8;

J Morris and D G Wishka, Synthesis, (1994), (1), 43–6;

Y Kobayashi et al, Chem Pharm Bull, (1971), 19(10), 2106–15;

K Novitskii et al, Khim Geterotskil Soedin, (1970) 2, 57–62; and

T Tsuchiya, J Kurita and K Takayama, Chem Pharm Bull, (1980), 28(9) 2676–81;

all incorporated herein by reference.

Certain intermediates described above are novel compounds, and it is to be understood that all novel intermediates herein form further aspects of the present invention. Compounds of formulae (II), (IV), (X) and (XVII) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples illustrate the invention but do not limit the invention in any way. All temperatures are in ° C. Flash column chromatography was carried out using Merck 9385 silica. Solid Phase Extraction (SPE) chromatography was carried out using Varian Mega Bond Elut (Si) cartridges (Anachem) under 15 mmHg vacuum with stepped gradient elution. Thin layer chromatography (Tlc) was carried out on silica plates. NMR was carried out on a Brucker 400 MHz spectrometer. Chemical shifts are given, with respect to tetramethylsilane as internal chemical shift reference, in δ ppm. In addition to those already defined, the following abbreviations are used: Me, methyl; DMSO, dimethylsulphoxide; TFA, trifluoroacetic acid; DME, dimethoxyethane; THF, tetrahydrofuran; DCM, dichloromethane; M, molar; s, singlet; d, doublet; t, triplet; m, multiplet; and br, broad.

EXAMPLE 1

4-[2-(3-Fluoro-phenyl)-6-trifluoromethyl-pyrazolo [1,5-a]pyridin-3-yl]benzenesulfonamide i) 3-Trifluoromethyl-pyridin-1-ylideneamine 2,4,6-trimethylphenylsulphonate Solid t-butoxycarbonyl-O-mesitylenesulfonylhydroxylamine (13.44 g, 42.5 mmol)[1] was added portionwise with stirring to TFA (40 ml) over 10 minutes then stirred for a further 30 minutes. The solution was poured onto ice (~250 ml) and left until the ice melted. The resulting white solid was filtered off, washed with water, and dissolved in DME (200 ml). The solution was dried over 4 Å mol. sieves for 1.5 hours, filtered, then 3-trifluoromethylpyridine (5 g, 34 mmol) added and the reaction stirred at ambient temperature for 20 h. The intermediate salt was isolated by filtration, washed with DME to give the title compound as a white solid (6.63 g, 54%). 1H NMR δ (DMSO) 9.34 (1H, s); 9.0 (1H, d, J 6 Hz); 8.8 (2H, br s); 8.68 (1H, d, J 8 Hz); 8.22 (1H, t, J 7 Hz); 6.75 (2H, s); 2.17 (3H, s).

Ref 1 Josef G Krause, Synthesis, 1972, 140 ii) 1-(2,2-Dibromo-vinyl)-3-fluoro-benzene

To a stirred, cooled (ice/salt, 0°) solution of carbon tetrabromide (48.82 g) in anhydrous DCM (200 ml) was added, portionwise over 3 minutes, triphenylphosphine (77.1 g), maintaining the temperature below 10°. The resulting orange suspension was stirred at 0° for 1 hour before adding to it 3-fluorobenzaldehyde (7.8 ml). After the addition was complete, the suspension was stirred at 0° for 1 hour then quenched by the addition of water (75 ml). The organic phase was separated and washed with brine (75 ml), dried ($Na_2SO_4$) and evaporated to dryness. The residue was poured into cyclohexane (1 L) and stirred for 30 minutes. The organic phase was decanted and the residue taken up into DCM and poured into cyclohexane (1 L). This procedure was repeated twice more and the combined organic phases concentrated to ~100 ml and passed through silica gel. The filtrate was concentrated to give the title compound as a mobile yellow oil (24 g, 100%). MH+ 280, MH− 279

NMR ($CDCl_3$) δ 7.05 (1H, tm, J=9 Hz) 7.3 (3H, m) 7.45 (1H, s).

iii) (3-Fluoro-phenyl)-propynoic acid methyl ester

To a stirred solution of 1-(2,2-dibromo-vinyl)-3-fluoro-benzene (23.8 g) in anhydrous THF (350 ml) cooled to −78° was added dropwise over 30 minutes, n-butyllithium (2.2 eq, 1.6M in hexanes). The mixture was stirred for a further 30 minutes at −78° before methyl chloroformate (11.6 g, 9.5 ml) was added and the resultant mixture allowed to warm to 0° for 1 hour before being diluted with 1:1 saturated aqueous sodium bicarbonate:ammonium chloride (100 ml) and extracted into ether (2×100 ml). The combined organic extract was washed with brine (25 ml), dried ($Na_2SO_4$) and evaporated to dryness to give the title compound as a brown oil (16.7 g, 100%). MH− 173

NMR (CDCl3) δ 7.4–7.1 (4H, m) 3.85 (3H, s, $CO_2Me$).

iv) 2-(3-Fluoro-phenyl)-6-trifluoromethyl-pyrazolo[1,5-a]pyridine-3-carboxylic acid methyl ester To a solution of (3-fluoro-phenyl)-propynoic acid methyl ester (1.75 g, 9.83 mmol) and 3-trifluoromethyl-pyridin-1-ylideneamine 2,4,6-trimethylphenylsulphonate (1.87 g, 5.17 mmol) in acetonitrile (15 ml) was added 1,8-diazabicyclo [5.4.0]undec-7-ene (1.47 ml) and the mixture heated to reflux for 30 minutes. The reaction was concentrated in vacuo, poured into water and extracted into ethyl acetate (2×50 ml). The combined organic phases were washed with water (20 ml), dried and purified by column chromatography with cyclohexane/ethyl acetate (20:1) as eluant. This gave the title compound as a white solid (448 mg, 26%).

1H NMR ($CDCl_3$) δ 8.9 (1H, s); 8.35 (1H, d, J 9 Hz); 7.60 (2H, 2xd, J 8 Hz); 7.55 (1H, d, J 10 Hz); 7.45 (1H, dt, J 8&6 Hz); 7.20 (1H, dt, J 8&2 Hz); 3.89 (3H, s).

v) 2-(3-Fluoro-phenyl)-6-trifluoromethyl-pyrazolo[1,5-a]pyridine-3-carboxylic acid To a suspension of 2-(3-fluoro-phenyl)-6-trifluoromethyl-pyrazolo[1,5-a]pyridine-3-carboxylic acid methyl ester (448 mg) in ethanol (10 ml) was added 2N sodium hydroxide and heated at reflux for 3 h. The cooled reaction mixture was acidified with 2N hydrochloric acid and the resulting solid isolated by filtration and dried in vacuo at 60° to give the title compound as an off-white solid (403 mg, 93%).

MH+=323

1H NMR (DMSO) δ 9.55 (1H, s); 8.3 (1H, d); 7.8 (1H, d); 7.65 (2H, 2xd); 7.55 (1H, m); 7.35 (1H, t).

vi) 3-Bromo-2-(3-fluoro-phenyl)-6-trifluoromethyl-pyrazolo[1,5-a]pyridine

To a solution of 2-(3-fluoro-phenyl)-6-trifluoromethyl-pyrazolo[1,5-a]pyridine-3-carboxylic acid (403 mg, 1.24 mmol) and $NaHCO_3$ (355 mg, 3.4 eq) in DMF (10 ml) was added NBS (1.1 eq, 244 mg) and the resulting solution stirred at rt for 1.5 h. The mixture was diluted with water and extracted with ethyl acetate (3×10 ml). The combined organic phases were washed with water (3×10 ml), dried and concentrated in vacuo to give the title compound as a brown solid (390 mg, 85%). MH+ 358/359

1H NMR (CDCl₃) 8.8 (1H, s); 7.9 (1H, d); 7.8 (1H, d); 7.65 (1H, d); 7.50 (1H, m); 7.35 (1H, d); 7.15 (1H, t).

vii) 4-[2-(3-Fluoro-phenyl)-6-trifluoromethyl-pyrazolo[1,5-a]pyridin-3-yl]benzenesulfonamide A mixture of 4-iodobenzenesulphonamide (651 mg); dipinacoldiborane (495 mg)²; potassium acetate (860 mg); and [1,1'-bis(diphenylphosphino)ferrocene]palladium(II) chloride complex:dichloromethane (1:1) (50 mg); in DMF (5 ml) was heated under nitrogen at 80° for 1.5 h. To the cooled reaction mixture was added 3-bromo-2-(3-fluoro-phenyl)-6-trifluoromethyl-pyrazolo[1,5-a]pyridine (330 mg, 0.919 mmol), 2N Na₂CO₃ (4 ml) and tetrakis(triphenylphosphine) palladium(0) (40 mg) and the mixture heated at reflux under nitrogen for 18 hours. The cooled reaction mixture was poured into water (30 ml) and the suspension extracted with ethyl acetate (3×20 ml). The organic extracts were combined, dried (Na₂SO₄) and concentrated in vacuo. The residue was purified by SPE chromatography eluting with a gradient of cyclohexane:ethyl acetate (100:0 to 0:100, 10% step). Trituration of the concentrated fractions containing product with diethyl ether gave the title compound as a white solid (139 mg, 35%). MH+ 436

1H (CDCl₃) 8.87 (1H, s); 8.0 (2H, d, J 8 Hz); 7.65 (1H, d, J 9 Hz); 7.50 (2H, d, J 8 Hz); 7.35 (4H, m); 7.10 (1H, t, J 8 Hz); 4.88 (2H, br s).

Ref 2: R. Miyaura et al J.Org.Chem., 1995, 60, 7508–7510

EXAMPLE 2

2-(3-Fluoro-phenyl)-3-(4-methanesulfonyl-phenyl)-6-trifluoromethyl-pyrazolo[1,5-a]pyridine To a solution of the 3-bromo-2-(3-fluoro-phenyl)-6-trifluoromethyl-pyrazolo[1,5-a]pyridine (50 mg, 0.139 mmol) in DMF (5 ml) was added 4-methanesulfonylphenylboronic acid (37 mg, 1.3 eq), ground potassium phosphate (83 mg) and tetrakis (triphenylphosphine)palladium(0) (10 mg) and the mixture heated to 90° for 18 h under N₂. The cooled mixture was poured into water (10 ml) and extracted into ethyl acetate (4×10 ml). The combined organic phases were washed sequentially with water, brine, 2N sodium hydroxide and brine, dried and concentrated in vacuo to give the title compound as an off-white solid (27 mg, 45%). MH+ 435

₁H NMR (CDCl₃) δ 8.9 (1H, s); 8.0 (2H, d, J 8 Hz); 7.65 (1H, d, J 9 Hz); 7.55 (2H, d, J 8 Hz); 7.25–7.4 (3H, m); 7.1 (1H, m); 3.15 (3H, s).

EXAMPLE 3

4-[2-(4-Ethoxy-phenyl)-6-trifluoromethyl-pyrazolo [1,5-a]pyridin-3-yl]benzenesulfonamide The process represented by Example 1(i)–(vii) was repeated, but substituting 4-ethoxybenzaldehyde for 3-fluorobenzaldehyde in step (ii). The title compound was obtained from 3-bromo-2-(4-ethoxy-phenyl)-6-trifluoromethyl-pyrazolo[1,5-a]pyridine in the manner described for Example 1(vii), as a white solid (127 mg, 44%).

MH+ 462

1H NMR (CDCl₃) δ 8.85 (1H, s); 7.95 (2H, d, J 8 Hz); 7.60 (1H, d, J 9 Hz); 7.52 (2H, d, 8 Hz); 7.47 (2H, d, J 8 Hz); 7.3 (1H, dd, J (&2 Hz); 6.9 (2H, d, J 9 Hz); 4.86 (2H, br s); 4.07 (2H, q, J 7 Hz); 1.45 (3H, t, J 7 Hz).

EXAMPLE 4

4-[2-(4-Fluoro-phenyl)-6-trifluoromethyl-pyrazolo [1,5-a]pyridin-3-yl]benzenesulfonamide The process represented by Example 1(i)–(vii), was repeated, but substituting 4-fluorobenzaldehyde for 3-fluorobenzaldehyde in step (ii). The title compound was obtained from 3-bromo-2-(4-fluoro-phenyl)-6-trifluoromethyl-pyrazolo[1,5-a]pyridine in the manner described for Example 1(vii), as a brown solid (240 mg, 70%).

MH+ 436

1H NMR (CDCl₃) δ 8.85 (1H, s); 8.0 (2H, d, J 8 Hz); 7.65 (1H, d, J 9 Hz); 7.5 (4H, m), 7.33 (1H, dd, J 9&1 Hz); 7.1 (2H, t, 8 Hz); 5.0 (2H, br s).

EXAMPLE 5

2-(4-Fluoro-phenyl)-3-(4-methanesulfonyl-phenyl)-6-trifluoromethyl-pyrazolo[1,5-a]pyridine By using 3-bromo-2-(4-fluoro-phenyl)-6-trifluoromethyl-pyrazolo[1,5-a]pyridine the title compound was obtained as a white solid (95 mg, 48%) in the manner described in Example 2.

MH+=435

1H NMR (CDCl₃) δ 8.87 (1H, s); 8.0 (2H, d, J 8 Hz); 7.67 (1H, d, J 9 Hz); 7.55 (4H, m); 7.35 (1H, dd, J 9&1 Hz); 7.1 (2H, t, J 9 Hz); 3.15 (3H, s).

EXAMPLE 6

4-(2-Phenyl-6-trifluoromethyl-pyrazolo[1,5-a] pyridin-3-yl)-benzenesulfonamide

The process represented by Example 1(i)–(vii), was repeated, but substituting propynoic acid methyl ester (Lancaster) for 3-fluoro-phenyl)-propynoic acid methyl ester in step (iv). The title compound was obtained from 3-bromo-2-phenyl-6-trifluoromethyl-pyrazolo[1,5-a] pyridine in the manner described for Example 1(vii), as a white solid (140 mg, 43%). MH+ 418

1H NMR (CDCl₃) δ 8.85 (1H, s); 7.95 (2H, d, J 8 Hz); 7.65 (1H, d, J 9 Hz) 7.53 (3H, m); 7.4 (4H, m) 4.86 (2H, br s).

EXAMPLE 7

3-(4-Methanesulfonyl-phenyl)-2-phenyl-6-trifluoromethyl-pyrazolo[1,5-a]pyridine

By using 3-bromo-2-phenyl-6-trifluoromethyl-pyrazolo [1,5-a]pyridine the title compound was obtained as an off-white solid (21 mg, 34%) in the manner described in Example 2. MH+ 417

1H NMR (CDCl₃) δ 8.87 (1H, s); 7.97 (2H, d, 8 Hz); 7.67 (1H, d, J 9 Hz); 7.55 (4H, m); 7.4 (4H, m); 3.15 (3H, s).

EXAMPLE 8

4-[2-(4-methyl-phenyl)-6-trifluoromethyl-pyrazolo [1,5-a]pyridin-3-yl]benzenesulfonamide The process represented by Example 1(i)–(vii), was repeated, but substituting 4-methylbenzaldehyde for 3-fluorobenzaldehyde in step (ii). The title compound was obtained from 3-bromo-2-(4-methyl-phenyl)-6-trifluoromethyl-pyrazolo[1,5-a]pyridine in the manner described for Example 1 (vii), as an off-white solid (168 mg, 36%). MH+ 432

1H CDCl₃ δ 8.85 (1H, s); 7.95 (2H, d, J 8 Hz); 7.63 (1H, d, J 9.3 Hz); 7.47 (2H, d, J 8 Hz); 7.44 (2H, d, J 8 Hz); 7.31 (1H, d, J 8 Hz); 7.18 (2H, d, J 8 Hz), 5.95 (2H, br s); 2.37 (3H, s).

EXAMPLE 9

N-Acetyl-4-[2-(3-fluorophenyl)-6-(trifluoromethyl)
pyrazolo[1,5-a]pyridin-3-yl]benzenesulfonamide A mixture of 4-[2-(3-fluoro-phenyl)-6-trifluoromethyl-pyrazolo[1,5-a]pyridin-3-yl]benzenesulfonamide (0.2 g, 0.46 mmol) and acetyl chloride (Aldrich) (1 ml) in acetic acid (1 ml) was heated at 95° for 1 hr. The solvent was removed and the resulting oil was dissolved in ethyl acetate (30 ml), washed with M $Na_2CO_3$ (10 ml) and brine (10 ml). Drying ($MgSO_4$) and removal of solvent gave a white solid which was triturated with 40–60 petroleum ether, filtered and dried to give the title compound (0.17 g 77%). MH– 476

NMR (DMSO-$d_6$): δ 1.82 (3H, s) 7.25–7.35 (3H, m) 7.45–7.52 (2H, m) 7.48 (2H, d) 7.55 (1H, d) 7.84 (1H, d) 7.89 (2H, d) 9.48 (1H, s).

EXAMPLE 10

N-Acetyl-4-[2-(4-ethoxyphenyl)-6-(trifluoromethyl)
pyrazolo[1,5-a]pyridin-3-yl]benzenesulfonamide By using 4-[2-(4-ethoxy-phenyl)-6-trifluoromethyl-pyrazolo[1,5-a]pyridin-3-yl]benzenesulfonamide (0.1 g 0.2 mmol), the title compound was obtained in the manner of Example 9 as a white solid (0.11 g 100%).

$MH^+$: 504

NMR ($CDCl_3$): δ 1.44 (3H, t) 2.25 (3H, s) 4.07 (2H, q) 6.90 (2H, d) 7.32 (1H, d) 7.60 (2H, d) 7.65 (2H, d) 8.07 (2H, d) 8.27 (1H, br) 8.85 (1H, s).

EXAMPLE 11

N-Acetyl-4-[2-phenyl-6-(trifluoromethyl)pyrazolo[1,
5-a]pyridin-3-yl]benzenesulfonamide By using 4-(2-phenyl-6-trifluoromethyl-pyrazolo[1,5-a]pyridin-3-yl)-benzenesulfonamide (0.1 g 0.2 mmol), the title compound was obtained in the manner of Example 9 as a light brown solid (0.11 g 100%).

$MH^+$: 460

NMR ($CDCl_3$) δ 2.30 (3H, s) 7.34 (1H, s) 7.37–7.42 (3H, m) 7.51–7.56 (4H, m) 7.69 (1H, d) 8.07 (2H, d) 8.18 (1H, br) 8.88 (1H, s).

EXAMPLE 12

Sodium salt of N-acetyl-4-[2-(3-fluorophenyl)-6-
(trifluoromethyl)pyrazolo[1,5-a]pyridin-3-yl]
benzenesulfonamide To a solution of N-acetyl-4-[2-(3-fluorophenyl)-6-(trifluoromethyl)pyrazolo[1,5-a]pyridin-3-yl]benzenesulfonamide (0.087 g 0.2 mmol) in ethanol (5 ml) was added 2M sodium hydroxide (0.1 ml 0.2 mmol) and the mixture was allowed to stand at room temperature for 15 minutes. Removal of solvent gave a white solid which was triturated with diethyl ether, filtered and dried to give the title compound (0.08 g 80%).

EXAMPLE 13

4-[2-(3-Fluorophenyl)-6-(trifluoromethyl)pyrazolo
[1,5-a]pyridin-3-yl]-N-(2-methoxyacetyl)
benzenesulfonamide To a solution of 4-[2-(3-fluoro-phenyl)-6-trifluoromethyl-pyrazolo[1,5-a]pyridin-3-yl]-benzenesulfonamide (0.15 g 0.35 mmol) in dry THF (3 ml) was added N,N-(diisopropyl) aminomethylpolystyrene (Argonaut Technologies) (0.25 g 0.9 mmol), 4-dimethylaminopyridine (Aldrich) (0.03 g 0.25 mmol) and methoxyacetyl chloride (Aldrich) (0.09 g 0.8 mmol) and the mixture was shaken at room temperature for 18 hr. Tris-(2-aminoethyl)amine polystyrene (Argonaut Technologies) (0.5 g 1.7 mmol) was added and shaking continued for 6 hr. The resins were filtered, washed with dichloromethane (5 ml) and the solvents were removed. The residue was purified by SPE chromatography eluting with cyclohexane:ethyl acetate (5:1 then 2:1) to give the title compound as a white solid. (0.07 g, 40%).

$MH^+$: 508

NMR ($CDCl_3$): δ 3.46 (3H, s) 3.94 (2H, s) 7.10 (1H, m) 7.25–7.38 (4H, m) 7.53 (2H, d) 7.68 (1H, d) 8.15 (2H, d) 8.86 (1H, s) 8.95 (1H, br).

EXAMPLE 14

4-[2-(3-Fluorophenyl)-6-(trifluoromethyl)pyrazolo
[1,5-a]pyridin-3-yl]-N-propionylbenzenesulfonamide By using propionyl chloride (Aldrich) (0.092 g 1 mmol) the title compound was obtained in the manner of Example 13 as a white solid (0.11 g 63%).

$MH^+$: 492

NMR ($CDCl_3$): δ 1.14 (3H, t) 2.36 (2H, q) 7.10 (1H, m) 7.25–7.40 (4H, m) 7.53 (2H, d) 7.68 (1H, d) 8.13 (2H, d) 8.20 (1H, br) 8.87 (1H, s).

EXAMPLE 15

4-[2-(3-Fluorophenyl)-6-(trifluoromethyl)pyrazolo
[1,5-a]pyridin-3-yl]-N-
isobutyrylbenzenesulfonamide By using isobutyryl chloride (Aldrich) (0.107 g 1 mmol) the title compound was obtained in the manner of Example 13 as a white solid (0.068 g 38%).

MH+: 506

NMR ($CDCl_3$): δ 1.15 (6H, d) 2.46 (1H, sept) 7.09 (1H, m) 7.25–7.40 (4H, m) 7.53 (2H, d) 7.68 (1H, d) 8.13 (2H, d) 8.45 (1H, br) 8.87 (1H, s).

EXAMPLE 16

N-Benzoyl-4-[2-(3-fluorophenyl)-6-(trifluoromethyl)
pyrazolo[1,5-a]pyridin-3-yl]benzenesulfonamide By using benzoyl chloride (Aldrich) (0.21 g 1.5 mmol) the title compound was obtained in the manner of Example 13 as a white solid (0.07 g 37%). $MH^+$: 540

NMR ($CD_3OD$): δ 6.98 (1H, m) 7.15–7.25 (3H, m) 7.27–7.35 (4H, m) 7.66 (1H, d) 7.40 (2H, d) 7.77 (2H, d) 7.99 (2H, d) 8.95 (1H, s).

EXAMPLE 17

Methyl 4-[({4-[2-(3-fluorophenyl)-6-
(trifluoromethyl)pyrazolo[1,5-a]pyridin-3-yl]
phenyl}sulfonyl)amino]-4-oxobutanoate By using 3-carbomethoxypropionyl chloride (Aldrich) (0.15 g 1 mmol) the title compound was obtained in the manner of Example 13 as a white solid (0.1 g 52%). $MH^+$: 550

NMR ($CDCl_3$): δ 2.64 (4H, m) 3.66 (3H, s) 7.10 (1H, m) 7.23–7.37 (4H, m) 7.52 (2H, d) 7.68 (1H, d) 8.11 (2H, d) 8.70 (1H, br) 8.86 (1H, s).

EXAMPLE 18

4-[({4-[2-(3-Fluorophenyl)-6-(trifluoromethyl)
pyrazolo[1,5-a]pyridin-3-yl]phenyl}sulfonyl)amino]-
4-oxobutanoic acid A solution of methyl 4-[({4-[2-(3-fluorophenyl)-6-(trifluoromethyl)pyrazolo[1,5-a]pyridin-3-yl]phenyl}sulfonyl)amino]-4-oxobutanoate (0.1 g 0.1 8 mmol) in methanol (20 ml) was heated under reflux with 2M sodium hydroxide (0.45 ml 0.9 mmol) for 24 hr. The solvent was removed and the resulting solid was dissolved in water (20 ml) and the pH was adjusted to 2 with 2M hydrochloric acid. The liberated solid was extracted into ethyl acetate (3×20 ml) and the combined extracts were washed with water (20 ml) and brine (20 ml). Drying (MgSO$_4$) and removal of solvent gave the title compound as a white solid (0.09 g 92%). MH$^+$: 536

NMR (CDCl$_3$): δ 2.62 (4H, m) 7.07 (1H, m) 7.22–7.37 (3H, m) 7.37 (1H, d) 7.53 (2H, d) 7.67 (1H, d) 8.10 (2H, d) 8.88 (1H, s) 9.04 (1H, br).

EXAMPLE 19

4-[2-(3-Fluorophenyl)-6-(trifluoromethyl)pyrazolo
[1,5-a]pyridin-3-yl]-N-
pentanoylbenzenesulfonamide To a solution of 4-[2-(3-fluoro-phenyl)-6-trifluoromethyl-pyrazolo[1,5-a]pyridin-3-yl]benzenesulfonamide (0.109 g 0.25 mmol) in chloroform (10 ml) was added diisopropyl-ethylamine (Aldrich) (100 µl), 4-dimethylaminopyridine (0.02 g 0.16 mmol) and valeryl chloride (Aldrich) (0.072 g 0.6 mmol) and the reaction was stirred at room temperature for 20 hr. It was washed with M Na$_2$CO$_3$ (5 ml), water (5 ml) and dried (MgSO$_4$). Removal of solvent gave a solid which was purified by SPE chromatography. Elution with cyclohexane:ethyl acetate (2:1) gave the title compound as a white solid (0.075 g 58%).

MH−: 518

NMR (Acetone-d$_6$): δ 0.77 (3H, t) 1.20 (2H, m) 1.45 (2H, m) 7.14 (1H, m) 7.23–7.42 (3H, m) 7.49 (1H, d) 7.58 (2H, d) 7.83 (1H, d) 8.04 (2H, d) 9.13 (1H, s).

EXAMPLE 20

2-[({4-[2-(3-Fluorophenyl)-6-(trifluoromethyl)
pyrazolo[1,5-a]pyridin-3-yl]phenyl}sulfonyl)amino]-
2-oxoethyl acetate By using 4-[2-(3-fluoro-phenyl)-6-trifluoromethyl-pyrazolo[1,5-a]pyridin-3-yl]benzenesulfonamide (0.15 g 0.35 mmol), diisopropylethylamine (Aldrich) (150 µl), 4-dimethylaminopyridine (0.04 g 0.32 mmol) and acetoxyacetyl chloride (Aldrich) (0.109 g 0.8 mmol), the title compound was obtained in the manner of Example 19 as a white solid (0.14 g 75%).

MH+: 536

NMR (CDCl$_3$): δ 2.05 (3H, s) 4.55 (2H, s) 6.94 (1H, m) 7.10–7.30 (6H, m) 7.46 (1H, d) 7.97 (2H, d) 8.75 (1H, s).

EXAMPLE 21

N-Acetyl-4-[2-(4-fluorophenyl)-6-(trifluoromethyl)
pyrazolo[1,5-a]pyridin-3-yl]benzenesulfonamide A solution of 4-[2-(4-fluoro-phenyl)-6-trifluoromethyl-pyrazolo[1,5-a]pyridin-3-yl]benzenesulphonamide (0.185 g 0.42 mmol), triethylamine (0.4 ml), 4-dimethylaminopyridine (0.024 g 0.18 mmol) and acetic anhydride (0.12 ml 1.2 mmol) in chloroform (10 ml) was stirred at room temperature for 4 hr. The reaction mixture was washed with 2M hydrochloric acid (10 ml), M Na$_2$CO$_3$ (5 ml) and water (10 ml). Drying (MgSO$_4$) and removal of solvent gave the title compound as a white solid (0.06 g 31%).

MH+ 478

NMR (CDCl$_3$): δ 2.05 (3H, s) 7.07 (2H, t) 7.34 (1H, d) 7.47 (2H, d) 7.55 (2H, m) 7.68 (1H, d) 8.05 (2H, d) 8.86 (1H, s).

EXAMPLE 22

N-(2-Chloroacetyl)-4-[2-(3-fluorophenyl)-6-
(trifluoromethyl)pyrazolo[1,5-a]pyridin-3-yl]
benzenesulfonamide By using 4-[2-(3-fluoro-phenyl)-6-trifluoromethyl-pyrazolo[1,5-a]pyridin-3-yl]benzenesulfonamide (0.7 g 1.6 mmol), triethylamine (1.6 ml), 4-dimethylaminopyridine (0.1 g 0.8 mmol) and chloroacetic anhydride (Aldrich) (0.825 g 4.8 mmol), the title compound was obtained the manner of Example 21 as a white solid (0.5 g 61%). MH−: 510, 512

NMR (CDCl$_3$): δ 4.08 (2H, s) 7.11 (1H, m) 7.30–7.40 (4H, m) 7.55 (2H, d) 7.68 (1H, d) 8.14 (2H, d) 8.87 (1H, s) 8.90 (1H, br).

EXAMPLE 23

N-[2-(Diethylamino)acetyl]-4-[2-(3-fluorophenyl)-6-
(trifluoromethyl)pyrazolo[1,5-a]pyridin-3-yl]
benzenesulfonamide A mixture of N-(2-chloroacetyl)-4-[2-(3-fluorophenyl)-6-(trifluoromethyl)pyrazolo[1,5-a]pyridin-3-yl]benzenesulfonamide (0.1 g 0.2 mmol), diethylamine (0.073 g 1 mmol) and sodium iodide (0.005 g 0.03 mmol) in dry THF (5 ml) was stirred at room temperature for 24 hr. The solvent was removed and the residues partitioned between ethyl acetate (10 ml) and water (10 ml). The organic layer was dried (MgSO$_4$), the solvent removed and the residues were purified by SPE chromatography using a cartridge containing an ion exchange sorbent that retains amino functionality. Elution with 5% acetic acid in methanol, ethyl acetate then 2M ammonia in methanol gave the title compound as a yellow solid (0.066 g 60%). MH+: 549

NMR (CDCl$_3$): δ 1.25 (6H, t) 3.12 (4H, q) 3.52 (2H, s) 7.05 (1H, m) 7.25–7.35 (4H, m) 7.44 (2H, d) 7.63 (1H, d) 8.08 (2H, d) 8.85 (1H, s).

Ref 3: e.g. an SCX containing cartridge (Isolute).

EXAMPLE 24

Methyl{4-[2-(3-fluorophenyl)-6-(trifluoromethyl)
pyrazolo[1,5-a]pyridin-3-yl]
phenyl}sulfonylcarbamate A Mixture of 4-[2-(3-fluoro-phenyl)-6-trifluoromethyl-pyrazolo[1,5-a]pyridin-3-yl]benzenesulfonamide (0.1 g 0.23 mmol), methyl chloroformate (Aldrich) (0.028 g 0.3 mmol) and potassium carbonate (0.07 g 0.05 mmol) were stirred and heated at reflux under nitrogen in acetone (10 ml) for 18 hr. Additional methyl chloroformate (0.028 g) and potassium carbonate (0.07 g) were added and heating continued for a further 24 hr. The reaction mixture was poured into water (100 ml) and extracted with ethyl acetate (3×50 ml). The combined extracts were washed with brine (30 ml), dried (MgSO$_4$) and the solvent removed. The residues were purified by SPE chromatography, elution with cyclohexane:ethyl acetate (3:1) gave the title compound as a white solid (0.03 g 26%). MH– 492

NMR (CDCl$_3$): δ 3.73 (3H, s) 7.10 (1H, m) 7.25–7.40 (4H, m) 7.52 (2H, d) 7.68 (1H, d) 8.06 (2H, d) 8.88 (1H, s).

EXAMPLE 25 tert-Butyl{4-[2-(3-fluorophenyl)-6-(trifluoromethyl)pyrazolo[1,5-a]pyridin-3-yl]phenyl}sulfonylcarbamate A Mixture of 4-[2-(3-fluoro-phenyl)-6-trifluoromethyl-pyrazolo[1,5-a]pyridin-3-yl]benzenesulfonamide (0.1 g 0.23 mmol), di-tert-butyl dicarbonate (Aldrich) (0.066 g 0.3 mmol) and 4-dimethylaminopyridine (0.004 g 0.03 mmol) were stirred in dry DCM (10 ml) containing triethylamine (100 µl) under nitrogen at room temperature for 2 hr. The reaction mixture was washed with 2M hydrochloric acid (10 ml), water (10 ml) and dried (MgSO$_4$). After removal of solvent the residues were purified by SPE chromatography, elution with cyclohexane:ethyl acetate (20:1) gave the title compound as a white solid (0.1 g 88%). MH$^+$: 536

NMR (CDCl$_3$): δ 1.44 (9H, s) 7.10 (1H, m) 7.25–7.40 (4H, m) 7.53 (2H, d) 7.66 (1H, d) 8.06 (2H, d) 8.88 (1H, s).

Examples 26–35 were prepared according to procedures described hereinabove.

EXAMPLE 26

4-[6-chloro-2-(3-ethoxyphenyl)pyrazolo[1,5-a]pyridin-3-yl]benzenesulfonamide

MH–, 426.

EXAMPLE 27

6-chloro-2-(3-ethoxyphenyl)-3-[4-(methylsulfonyl)phenyl]pyrazolo[1,5-a]pyridine

MH+, 427.

EXAMPLE 28

4-[6-methyl-2-phenyl-pyrazolo[1,5-a]pyridin-3-yl]benzenesulfonamide

MH+, 364.

EXAMPLE 29

4-[2-(3-fluorophenyl)-6-methyl-pyrazolo[1,5-a]pyridin-3-yl]benzenesulfonamide

MH+, 382.

EXAMPLE 30

4-[2-(3-ethoxyphenyl)-6-methyl-pyrazolo[1,5-a]pyridin-3-yl]benzenesulfonamide

MH+, 408.

EXAMPLE 31

4-[2-(4-ethoxyphenyl)-6-methyl-pyrazolo[1,5-a]pyridin-3-yl]benzenesulfonamide

MH+, 408.

EXAMPLE 32

6-methyl-2-phenyl-3-[4-(methylsulfonyl)phenyl]pyrazolo[1,5-a]pyridine

MH+, 363.

EXAMPLE 33

2-(3-fluorophenyl)-6-methyl-3-[4-(methylsulfonyl)phenyl]pyrazolo[1,5-a]pyridine

MH+, 381.

EXAMPLE 34

2-(3-ethoxyphenyl)-6-methyl-3-[4-(methylsulfonyl)phenyl]pyrazolo[1,5-a]pyridine

MH+, 407.

EXAMPLE 35

2-(4-ethoxyphenyl)-6-methyl-3-[4-(methylsulfonyl)phenyl]pyrazolo[1,5-a]pyridine

MH+, 407.

EXAMPLE 36

Tablets

| a) | | |
|---|---|---|
| | Compound of the invention | 5.0 mg |
| | Lactose | 95.0 mg |
| | Microcrystalline Cellulose | 90.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | | |
|---|---|---|
| | Compound of the invention | 5.0 mg |
| | Lactose | 165.0 mg |
| | Pregelatinised Starch | 20.0 mg |
| | Cross-linked polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 37

Capsules

| a) | Compound of the invention | 5.0 mg |
|---|---|---|
| | Lactose | 193.0 mg |
| | Magnesium Stearate | 2.0 mg |
| | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) | Compound of the invention | 5.0 mg |
|---|---|---|
| | Lactose | 177.0 mg |
| | Polyvinylpyrrolidone | 8.0 mg |
| | Cross-linked polyvinylpyrrolidone | 8.0 mg |
| | Magnesium Stearate | 2.0 mg |
| | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

EXAMPLE 38

Syrup

| a) | Compound of the invention | 5.0 mg |
|---|---|---|
| | Hydroxypropyl Methylcellulose | 45.0 mg |
| | Propyl Hydroxybenzoate | 1.5 mg |
| | Butyl Hydroxybenzoate | 0.75 mg |
| | Saccharin Sodium | 5.0 mg |
| | Sorbitol Solution | 1.0 ml |
| | Suitable Buffers | qs |
| | Suitable flavours | qs |
| | Purified Water to | 10.0 ml |

The hydroxypropyl methylcellulose is dispersed in a portion of hot purified water together with the hydroxybenzoates and the solution is allowed to cool to ambient temperature. The saccharin, sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

EXAMPLE 39

Injection Formulation

| | % w/v |
|---|---|
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 10 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.5, 2.0 and 5% w/v of the compound of the invention, so as to provide respectively 5, 20 and 50 mg/ml of the compound of the invention.

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 cm$^2$ flasks in which they were grown, onto 24-well cell culture plates using the following procedure. The incubation medium (Dulbecco's modified eagles medium (DMEM) supplemented with heat-inactivated foetal calf serum (10%v/v), penicillin (100 IU/ml), streptomycin (100 µg/ml) and geneticin (600 µg/ml)) was removed from a flask of confluent cells (1 flask at confluency contains approximately 1×10$^7$ cells). 10 ml of phosphate buffered saline (PBS) was added to the flask to wash the cells. Having discarded the PBS, cells were then rinsed in 10 ml trypsin for 20 seconds, after which the trypsin was removed and the flask placed in an incubator (37°) for 1–2 minutes until cells became detached from the flask. The flask was then removed from the incubator and cells resuspended in 10 ml of fresh incubation medium. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% $CO_2$) overnight. If more than 1 flask of cells were required, the cells from flasks were combined before being dispensed into the 24-well plates.

Following the overnight incubation, the incubation medium was completely removed from the 24-well cell culture plates and replaced with 250 µl fresh DMEM (37° C.). The test compounds were made up to 250× the required test concentration in DMSO and were added to the wells in a volume of 1 µl. Plates were then mixed gently by swirling and then placed in an incubator for 1 hour (37° C., 95% air/5% $CO_2$). Following the incubation period, 10 µl of arachidonic acid (750 µM) was added to each well to give a final arachidonic acid concentration of 30 µM. Plates were then incubated for a further 15 minutes, after which the incubation medium was removed from each well of the plates and stored −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values. The following $IC_{50}$ values for inhibition of COX-2 and COX-1 were obtained for compounds of the invention:

| Example No. | COX-2: $IC_{50}$ (nM) | COX-1: $IC_{50}$ (nM) |
|---|---|---|
| 1(vii) | 34 | >100,000 |
| 2 | 548 | >100,000 |
| 3 | 34 | 32,200 |
| 4 | 34 | >100,000 |
| 5 | 26 | >100,000 |
| 6 | 31 | 26350 |
| 7 | 30 | >100,000 |

What is claimed is:

1. A compound of formula (I)

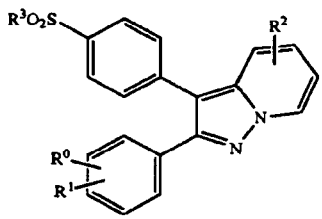

(I)

or a pharmaceutically acceptable salt thereof wherein $R^0$ and $R^1$ are independently selected from the group consisting of H, halogen, $C_{1-6}$alkyl, $C_{1-6}$alkoxy, and $C_{1-6}$alkoxy substituted by one or more fluorine atoms;

$R^2$ is selected from the group consisting of H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, C(O)H, $C(O)C_{1-6}$alkyl, $C_{1-6}$alkylsulphonyl, and $C_{1-6}$alkoxy substituted by one or more fluorine atoms; and $R^3$ is $C_{1-6}$alkyl or $NH_2$.

2. A compound as claimed in claim 1 wherein $R^0$ and $R^1$ are independently selected from the group consisting of H, halogen, $C_{1-6}$alkyl, and $C_{1-6}$alkoxy; $R^2$ is $C_{1-3}$alkyl substituted by one or more fluorine atoms; and $R^3$ is $C_{1-3}$alkyl or $NH_2$.

3. A compound as claimed in claim 1 wherein $R^0$ and $R^1$ are independently selected from the group consisting of H, F, Cl, $C_{1-3}$alkyl, and $C_{1-3}$alkoxy; $R^2$ is $C_{1-3}$alkyl substituted by one or more fluorine atoms; and $R^3$ is methyl or $NH_2$.

4. A compound as claimed in claim 1 wherein $R^0$ is selected from the group consisting of F, Cl, $C_{1-3}$alkyl and $C_{1-3}$alkoxy; $R^1$ is H; $R^2$ is $C_{1-3}$alkyl substituted by one or more fluorine atoms; and $R^3$ is methyl or $NH_2$.

5. A compound as claimed in claim 1 wherein $R^0$ is at the 3- or 4-position of the phenyl ring; and $R^2$ is at the 6-position of the pyridine ring.

6. The compound according to claim 1, wherein $R^0$ is selected from the group consisting of F, Cl, methyl and ethoxy; $R^1$ is H; $R^2$ is trifluoromethyl; and $R^3$ is methyl or $NH_2$.

7. A compound selected from the group consisting of:

4-[2-(3-fluoro-phenyl)-6-trifluoromethyl-pyrazolo[1,5-a]pyridin-3-yl]benzenesulfonamide;

2-(3-fluoro-phenyl)-3-(4-methanesulfonyl-phenyl)-6-trifluoromethyl-pyrazolo[1,5-a]pyridine;

4-[2-(4-ethoxy-phenyl)-6-trifluoromethyl-pyrazolo[1,5-a]pyridin-3-yl]benzenesulfonamide;

4-[2-(4-fluoro-phenyl)-6-trifluoromethyl-pyrazolo[1,5-a]pyridin-3-yl]benzenesulfonamide;

2-(4-fluoro-phenyl)-3-(4-methanesulfonyl-phenyl)-6-trifluoromethyl-pyrazolo[1,5-a]pyridine;

4-(2-phenyl-6-trifluoromethyl-pyrazolo[1,5-a]pyridin-3-yl)-benzenesulfonamide;

3-(4-methanesulfonyl-phenyl)-2-phenyl-6-trifluoromethyl-pyrazolo[1,5-a]pyridine;

4-[2-(4-methyl-phenyl)-6-trifluoromethyl-pyrazolo[1,5-a]pyridin-3-yl]benzenesulfonamide;

or a pharmaceutically acceptable salt thereof.

8. A compound selected from the group consisting of:

N-acetyl-4-[2-(3-fluorophenyl)-6-(trifluoromethyl)pyrazolo[1,5-a]pyridin-3-yl]benzenesulfonamide;

N-acetyl-4-[2-(4-ethoxyphenyl)-6-(trifluoromethyl)pyrazolo[1,5-a]pyridin-3-yl]benzenesulfonamide;

N-acetyl-4-[2-phenyl-6-(trifluoromethyl)pyrazolo[1,5-a]pyridin-3-yl]benzenesulfonamide;

sodium salt of N-acetyl-4-[2-(3-fluorophenyl)-6-(trifluoromethyl)pyrazolo[1,5-a]pyridin-3-yl]benzenesulfonamide;

4-[2-(3-fluorophenyl)-6-(trifluoromethyl)pyrazolo[1,5-a]pyridin-3-yl]-N-(2-methoxyacetyl)benzenesulfonamide;

4-[2-(3-fluorophenyl)-6-(trifluoromethyl)pyrazolo[1,5-a]pyridin-3-yl]-N-propionylbenzenesulfonamide;

4-[2-(3-fluorophenyl)-6-(trifluoromethyl)pyrazolo[1,5-a]pyridin-3-yl]-N-isobutyrylbenzenesulfonamide;

N-benzoyl-4-[2-(3-fluorophenyl)-6-(trifluoromethyl)pyrazolo[1,5-a]pyridin-3-yl]benzenesulfonamide;

methyl 4-[({4-[2-(3-fluorophenyl)-6-(trifluoromethyl)pyrazolo[1,5-a]pyridin-3-yl]phenyl}sulfonyl)amino]-4-oxobutanoate;

4-[({4-[2-(3-fluorophenyl)-6-(trifluoromethyl)pyrazolo[1,5-a]pyridin-3-yl]phenyl}sulfonyl)amino]-4-oxobutanoic acid;

4-[2-(3-fluorophenyl)-6-(trifluoromethyl)pyrazolo[1,5-a]pyridin-3-yl]-N-pentanoylbenzenesulfonamide;

2-[({4-[2-(3-fluorophenyl)-6-(trifluoromethyl)pyrazolo[1,5-a]pyridin-3-yl]phenyl}sulfonyl)amino]-2-oxoethyl acetate;

N-acetyl-4-[2-(4-fluorophenyl)-6-(trifluoromethyl)pyrazolo[1,5-a]pyridin-3-yl]benzenesulfonamide;

N-(2-chloroacetyl)-4-[2-(3-fluorophenyl)-6-(trifluoromethyl)pyrazolo[1,5-a]pyridin-3-yl]benzenesulfonamide;

N-[2-(diethylamino)acetyl]-4-[2-(3-fluorophenyl)-6-(trifluoromethyl)pyrazolo[1,5-a]pyridin-3-yl]benzenesulfonamide;

methyl{4-[2-(3-fluorophenyl)-6-(trifluoromethyl)
pyrazolo[1,5-a]pyridin-3-yl]
phenyl}sulfonylcarbamate; and tert-butyl{4-[2-(3-fluorophenyl)-6-(trifluoromethyl)
pyrazolo[1,5-a]pyridin-3-yl]
phenyl}sulfonylcarbamate.

9. A compound selected from the group consisting of:

4-[6-chloro-2-(3-ethoxyphenyl)pyrazolo[1,5-a]pyridin-3-yl]benzenesulfonamide;

6-chloro-2-(3-ethoxyphenyl)-3-[4-(methylsulfonyl)phenyl]pyrazolo[1,5-a]pyridine;

4-[6-methyl-2-phenyl-pyrazolo[1,5-a]pyridin-3-yl] benzenesulfonamide;

4-[2-(3-fluorophenyl)-6-methyl-pyrazolo[1,5-a]pyridin-3-yl]benzenesulfonamide;

4-[2-(3-ethoxyphenyl)-6-methyl-pyrazolo[1,5-a]pyridin-3-yl]benzenesulfonamide;

4-[2-(4-ethoxyphenyl)-6-methyl-pyrazolo[1,5-a]pyridin-3-yl]benzenesulfonamide;

6-methyl-2-phenyl-3-[4-(methylsulfonyl)phenyl]pyrazolo[1,5-a]pyridine;

2-(3-fluorophenyl)-6-methyl-3-[4-(methylsulfonyl)phenyl]pyrazolo[1,5-a]pyridine;

2-(3-ethoxyphenyl)-6-methyl-3-[4-(methylsulfonyl)phenyl]pyrazolo[1,5-a]pyridine;

2-(4-ethoxyphenyl)-6-methyl-3-[4-(methylsulfonyl)phenyl]pyrazolo[1,5-a]pyridine;

or a pharmaceutically acceptable salt thereof.

10. 4-[2-(3-fluoro-phenyl)-6trifluoromethyl-pyrazolo[1,5-a]pyridin-3-yl]benzenefulfonamide.

11. A pharmaceutical composition comprising a compound as claimed in claim 1 in admixture with one or more physiologically acceptable carriers or excipients.

12. A process for the preparation of a compound as claimed in claim 1, said process comprising the steps of:

(A) reacting a compound of formula (II)

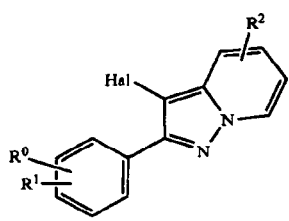

(II)

or a protected derivative thereof, with a compound of formula (III)

(III)

or a protected derivative thereof to prepare a compound of formula (I); and (B) optionally converting the compound of formula (I) to a pharmaceutically acceptable salt thereof.

13. A process for the preparation of a compound as claimed in claim 1, said process comprising the steps of:

(A) where $R^3$ represents $C_{1-4}$alkyl, reacting a compound of formula IV)

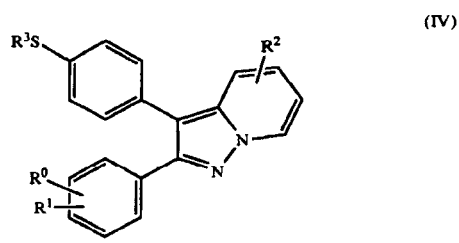

(IV)

or a protected derivative thereof with an oxidising agent to prepare a compound of formula (I); and (B) optionally converting the compound of formula (I) to a pharmaceutically acceptable salt thereof.

14. A process for the preparation of a compound as claimed in claim 1, said process comprising the steps of:

(A) where $R^2$ is $C_{1-6}$alkylsulphonyl, oxidising a compound of formula (V)

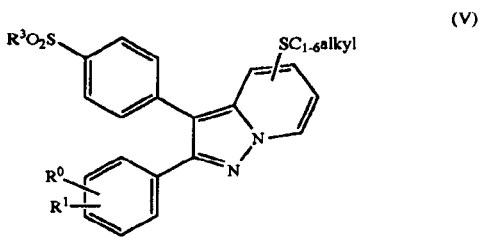

(V)

or a protected derivative thereof to prepare a compound of formula (I); and (B) optionally converting the compound of formula (I) to a pharmaceutically acceptable salt thereof.

15. A process for the preparation of a compound as claimed in claim 1, said process comprising the steps of:

(A) where $R^2$ is $C_{1-6}$alkoxy substituted by one or more fluorine atoms, reacting a alcohol of formula (VI)

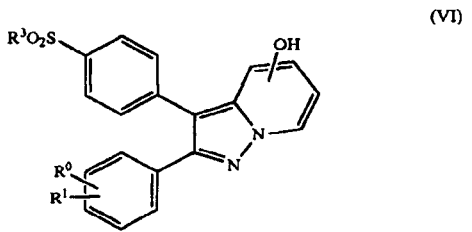

(VI)

or a protected derivative thereof with a halofluoroalkane to prepare a compound of formula (I); and (B) optionally converting the compound of formula (I) to a pharmaceutically acceptable salt thereof.

16. A process for the preparation of a compound as claimed in claim 1, said process comprising the steps of:
(A) where $R^3$ is $NH_2$, reacting a compound of formula (X)

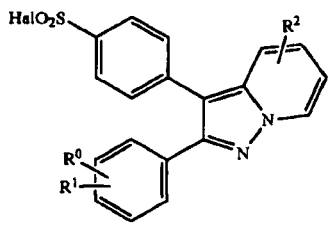

(X)

with a source of ammonia under conventional conditions to prepare a compound of formula (I); and
(B) optionally converting the compound of formula (I) to a pharmaceutically acceptable salt thereof.

17. A process for the preparation of a compound as claimed in claim 1, said process comprising the steps of:
(A) interconverting a compound of formula (I) into another compound of formula (I); and
(B) optionally converting the compound of formula (I) to a pharmaceutically acceptable salt thereof.

18. A process for the preparation of a compound as claimed in claim 1, said process comprising the steps of:
(A) deprotecting a protected derivative of compound of formula (I); and
(B) optionally converting the compound of formula (I) to a pharmaceutically acceptable salt thereof.

19. A method for the treatment of a human subject suffering from a condition or disease selected from the group consisting of pain, fever and inflammation, said method comprising administering an effective amount of a compound as claimed in claim 1.

20. A method for the treatment of a human subject suffering from pain, said method comprising administering an effective amount of a compound of formula (I) as claimed in claim 1.

21. The method of claim 19 wherein the human subject is suffering from the pain or inflammation of arthritis.

22. The method of claim 19 wherein the human subject is suffering from the pain or inflammation of lower back pain.

23. The method of claim 19 wherein the human subject is suffering from the pain or inflammation of neck pain.

24. The method of claim 19 wherein the human subject is suffering from the pain or inflammation of rheumatoid arthritis.

25. The method of claim 19 wherein the human subject is suffering from the pain or inflammation of osteoarthritis.

26. The method of claim 19 wherein the human subject is suffering from the pain, fever or inflammation of dysmenorrhoea.

* * * * *